(12) United States Patent
Lewis et al.

(10) Patent No.: US 6,537,498 B1
(45) Date of Patent: Mar. 25, 2003

(54) COLLOIDAL PARTICLES USED IN SENSING ARRAYS

(75) Inventors: Nathan S. Lewis, La Canada, CA (US); Brett J. Doleman, San Francisco, CA (US); Shawn Briglin, Pasadena, CA (US); Erik J. Severin, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/328,871

(22) Filed: Jun. 8, 1999

Related U.S. Application Data

(63) Continuation-in-part of application No. 08/986,500, filed on Jan. 4, 2000, now Pat. No. 6,010,616, which is a continuation of application No. 08/689,227, filed on Dec. 16, 1997, now Pat. No. 5,698,089, which is a continuation of application No. 08/410,809, filed on Mar. 27, 1995, now Pat. No. 5,571,401.

(60) Provisional application No. 60/088,630, filed on Jun. 9, 1998, and provisional application No. 60/118,833, filed on Feb. 5, 1999.

(51) Int. Cl.[7] .................. G01N 27/00; G01N 27/02; G01N 27/327

(52) U.S. Cl. ................ 422/82.01; 422/82.02; 422/82.05; 422/68.1; 422/98; 204/403.01

(58) Field of Search .................. 204/403, 416, 204/412, 400, 403.01; 422/82.01, 82.02, 68.1, 82.05

(56) References Cited

U.S. PATENT DOCUMENTS

| 3,927,930 A | 12/1975 | Goldberg et al. |
|---|---|---|
| 4,453,126 A | 6/1984 | Volgyesi |
| 4,644,101 A | 2/1987 | Jin et al. |
| 4,737,112 A | 4/1988 | Jin et al. |
| 4,923,739 A | 5/1990 | Jin et al. |
| 4,980,541 A * | 12/1990 | Shafe et al. ............... 219/548 |
| 5,104,210 A | 4/1992 | Tokas |
| 5,298,783 A * | 3/1994 | Xinghui ..................... 257/414 |
| 5,429,975 A | 7/1995 | Sheu et al. |
| 5,451,920 A * | 9/1995 | Hoffheins et al. ........... 338/34 |
| 5,512,882 A | 4/1996 | Stetter et al. |
| 5,571,401 A | 11/1996 | Lewis et al. |
| 5,677,662 A | 10/1997 | Bresolin et al. |

(List continued on next page.)

FOREIGN PATENT DOCUMENTS

WO   WO 99/273557   6/1999   ......... G01N/27/327

OTHER PUBLICATIONS

Burst et al., "Synthesis of Thiol–derviatised Gold Nanoparticles in a Two–phase Liquid–Liquid System," *J. Chem. Soc., Chem. Commun.*, 801–802 (1996).

Henglein, Arnim, "Physicochemical Properties of Small Metal Particles in Solution: 'Microelectrode' Reactions, Chemisorption, Composite Metal Particles, and the Atom–to–Metal Transition," *J. Phys. Chem.*, 97(21):5457–5471 (1993).

(List continued on next page.)

*Primary Examiner*—Jill Warden
*Assistant Examiner*—Alex Noguerola
(74) *Attorney, Agent, or Firm*—Townsend and Townsend and Crew, LLP

(57) ABSTRACT

Chemical sensors for detecting analytes in fluids comprising a plurality of alternating nonconductive regions (comprising a nonconductive material) and conductive regions (comprising a conductive material). In preferred embodiments, the conducting region comprises a nanoparticle. Variability in chemical sensitivity from sensor to sensor is provided by qualitatively or quantitatively varying the composition of the conductive and/or nonconductive regions. An electronic nose for detecting an analyte in a fluid may be constructed by using such arrays in conjunction with an electrical measuring device electrically connected to the conductive elements of each sensor.

15 Claims, 10 Drawing Sheets

U.S. PATENT DOCUMENTS

| | | | |
|---|---|---|---|
| 5,698,771 A | | 12/1997 | Shields et al. |
| 5,742,223 A | | 4/1998 | Simendinger, III et al. |
| 5,922,537 A | * | 7/1999 | Ewart et al. .................... 435/6 |
| 5,942,674 A | | 8/1999 | Logothetis et al. |
| 6,002,817 A | * | 12/1999 | Kopelman et al. ............ 385/12 |
| 6,202,471 B1 | * | 3/2001 | Yadav et al. ................ 73/31.05 |

OTHER PUBLICATIONS

Hostetler et al., "Monolayers in Three Dimenisons: Synthesis and Electrochemistry of ω–Functionalized Alkanethiolate–Stabilized Gold Cluster Compounds," *J. Am. Chem. Soc.* 118:4212–4213 (1996).

Hostetler et al., "Alkanethiolate Gold Cluster Molecules with Core Diameters from 1.5 to 5.2nm: Core and Monolayer Properties as a Function of Core Size," *Langmuir*, 14:17–30 (1998).

Ingram et al., "Poly–hetero–ω–functionlized Alkanethiolate–Stabilized Gold Cluster Compounds," *J. Am. Chem. Soc.*, 119:9175–9178 (1997).

Leff et al., "Thermodyamic Control of Gold Nanocrystal Size: Experimental and Theorpy," 99:7036–7041 (1995).

Leff et al., "Synthesis and Characterization of Hydrophobic, Organically–Soluble Gold Nanocrystals Functionlized with Primary Amines," *Langmuir*, 12:4723–4730 (1996).

Lonergan et al., "Array–Based Vapor Sensing Using Chemically Sensitive, Carbon Black–Polymer Resistors," *Chem. Mater.*, 8:2298–2312 (1996).

Luedtke, W.D. and Landman, Uzi, "Structure, Dynamics, and Thermodynamics of Passivated Gold Nanocrystallites and Their Assemblies," *J. Phys. Chem.*, 100(32):13323–13329 (1996).

Snow, Arthur W. and Wohltjen, Hank, "Size–Induced Metal to Semiconductor Transition in a Stabilized Gold Cluster Ensemble," *Chem. Mater.*, 10(4):947–949 (Apr. 1998).

Templeton et al., "Reactivity of Monolayer–Protected Gold Cluster Molecules: Steric Effects," *J. Am. Chem. Soc.*, 120:1906–1911 (1998).

Terrill et al., "Monolayers in Three Dimensions: NMR, SAXS, Thermal, and Electron Hopping Studies of Alkanethiol Stablized Gold Clusters," *J. Am. Chem. Soc.*, 117:12357–12548 (1995).

Wohltjen, Hank and Snow, Arthur W., "Colloidal Metal–Insulator–Metal Ensemble Chemiresistor Sensor," *Anatytical Chemistry*, 70(14):2856–2859 (1998).

Zeiri, Leila and Efrima Shlomo, "Studies of Silver Organosols: Preparation, Characterization, and Cyanide–Induced Aggregation," *J. Phys. Chem.*, 96:5908–5917 (1992).

Grate et al. "Role of Selective Sorption in Chemiresistor Sensors for Organophosphorus Detection", Analytical Chemistry 62:1927–1934 (Sep. 1990) .

* cited by examiner

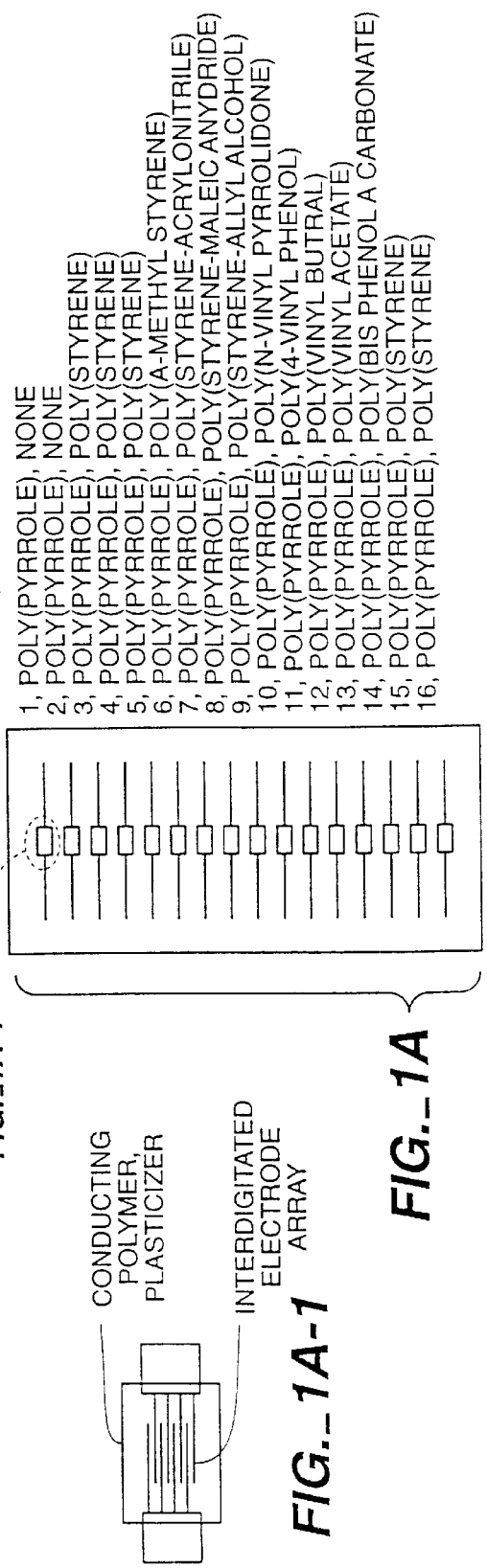
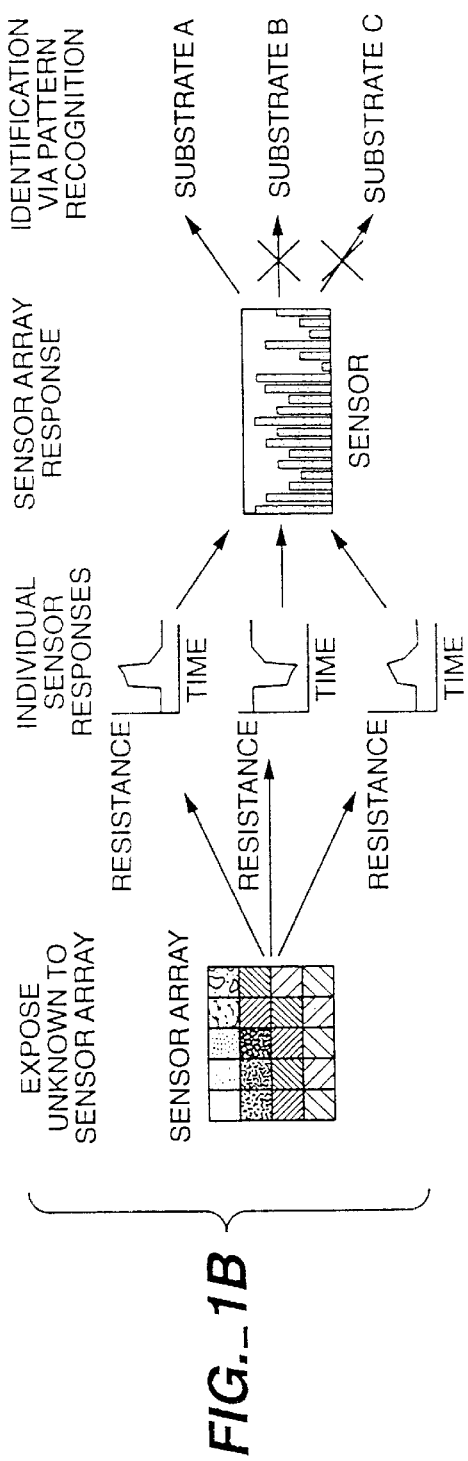
FIG._1A-1
FIG._1A
FIG._1B

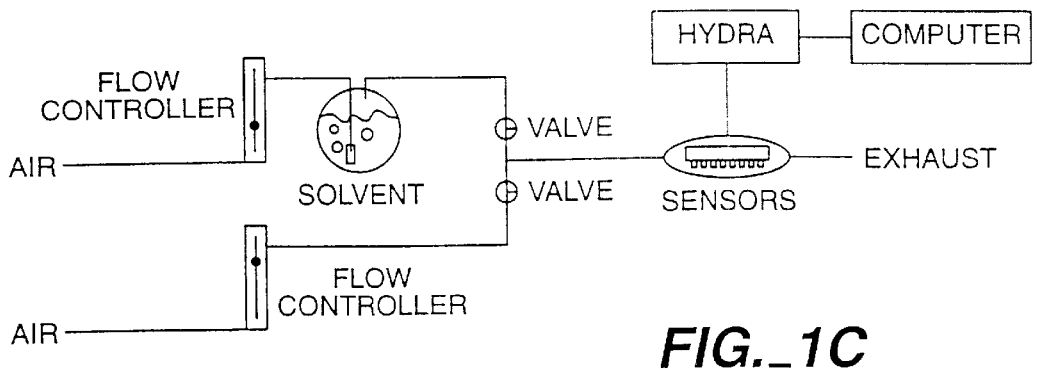
FIG._1C
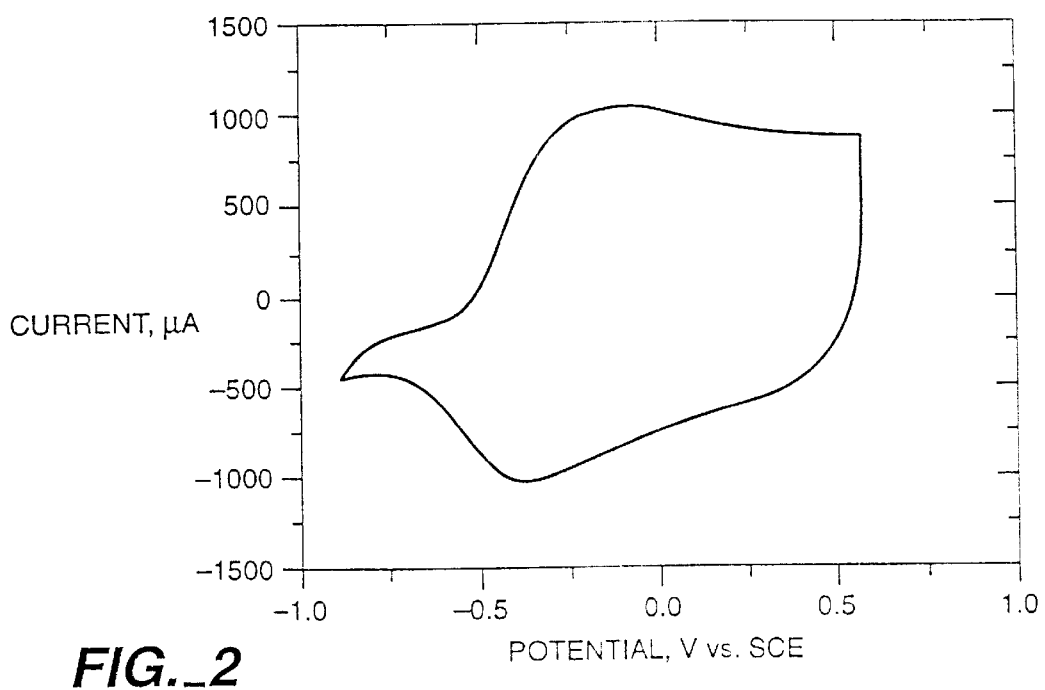
FIG._2

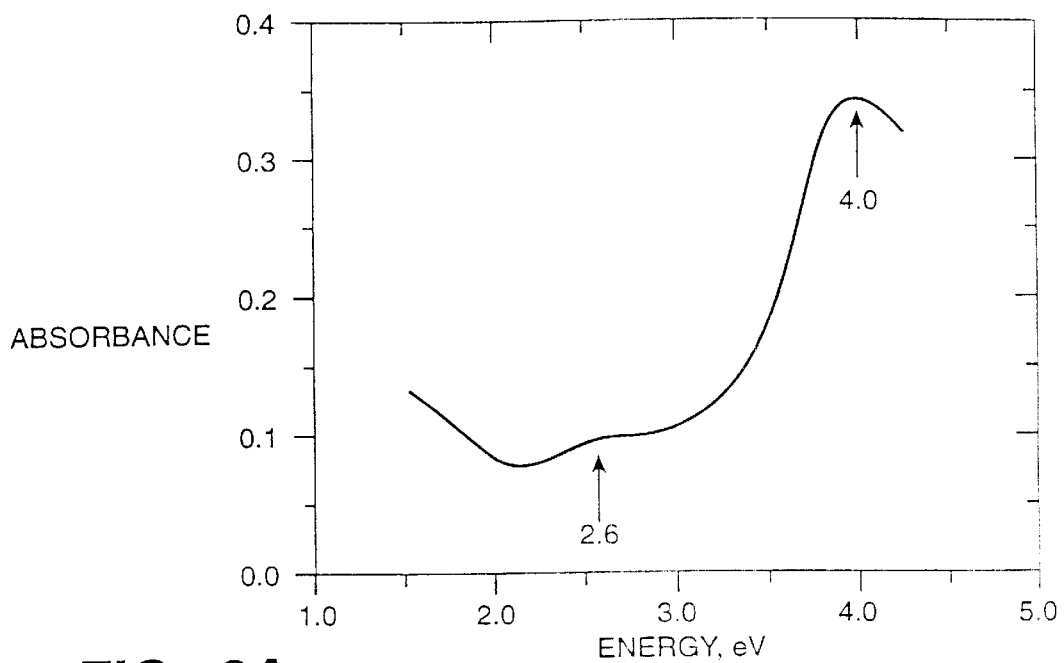
FIG._3A
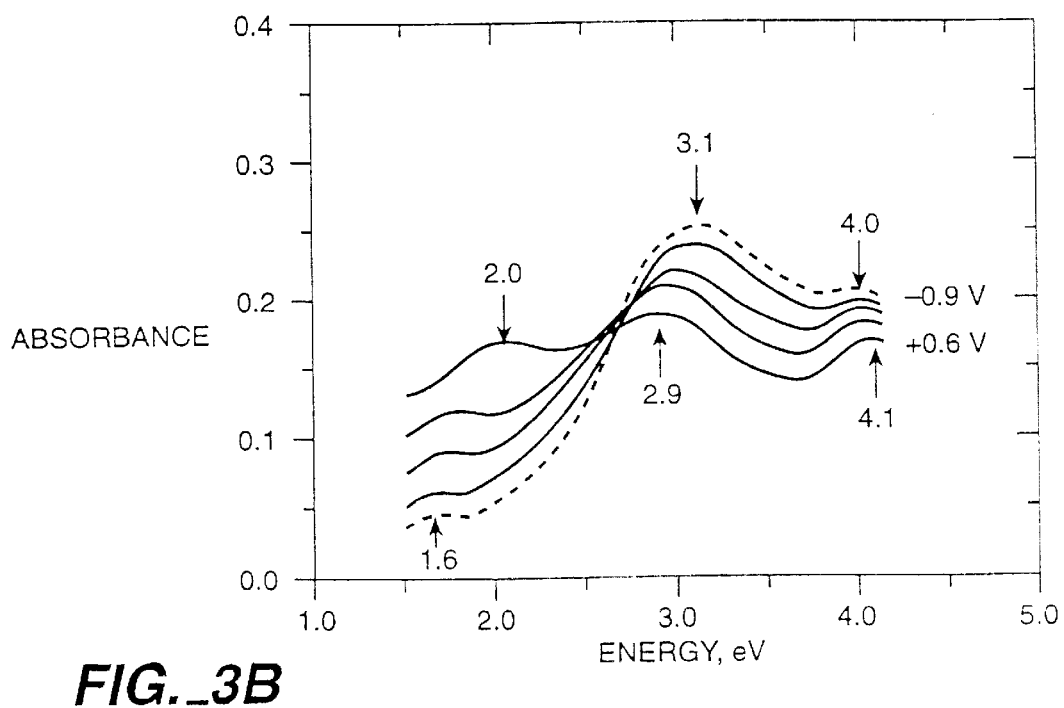
FIG._3B

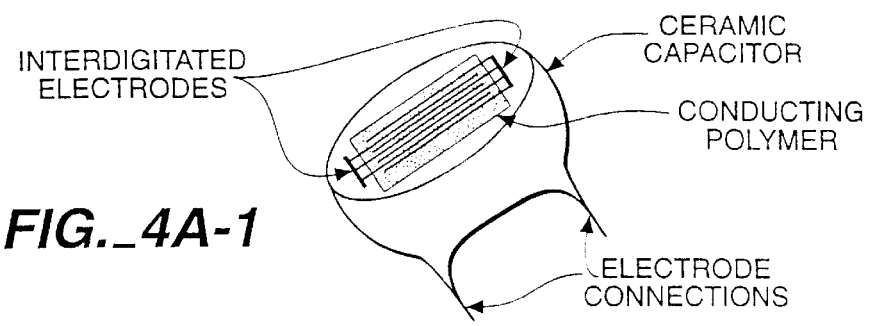
FIG._4A-1
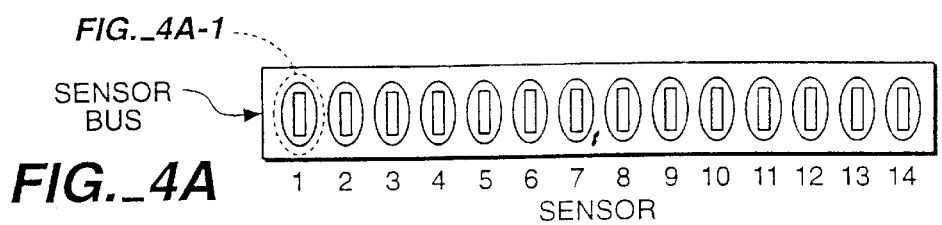
FIG._4A
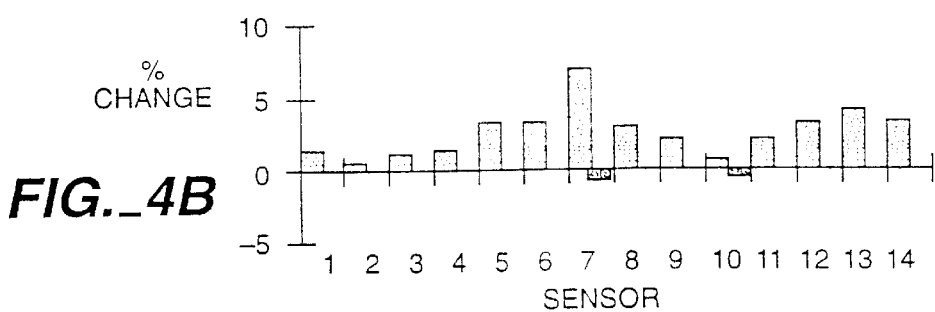
FIG._4B
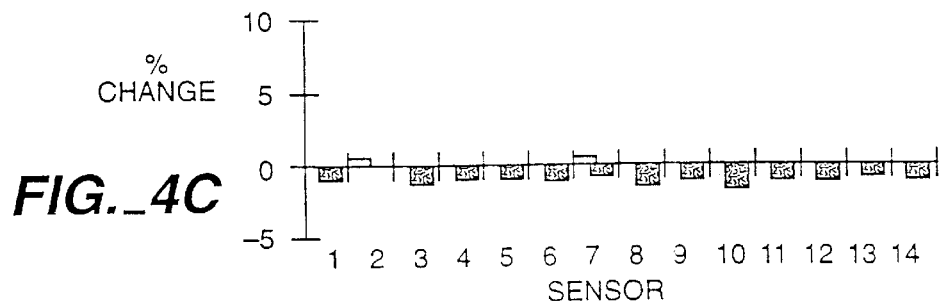
FIG._4C
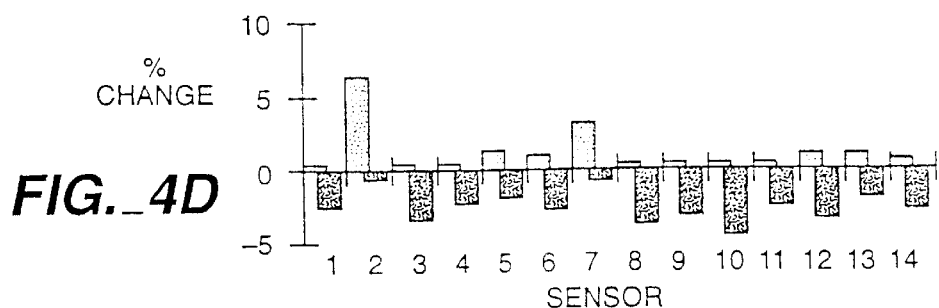
FIG._4D

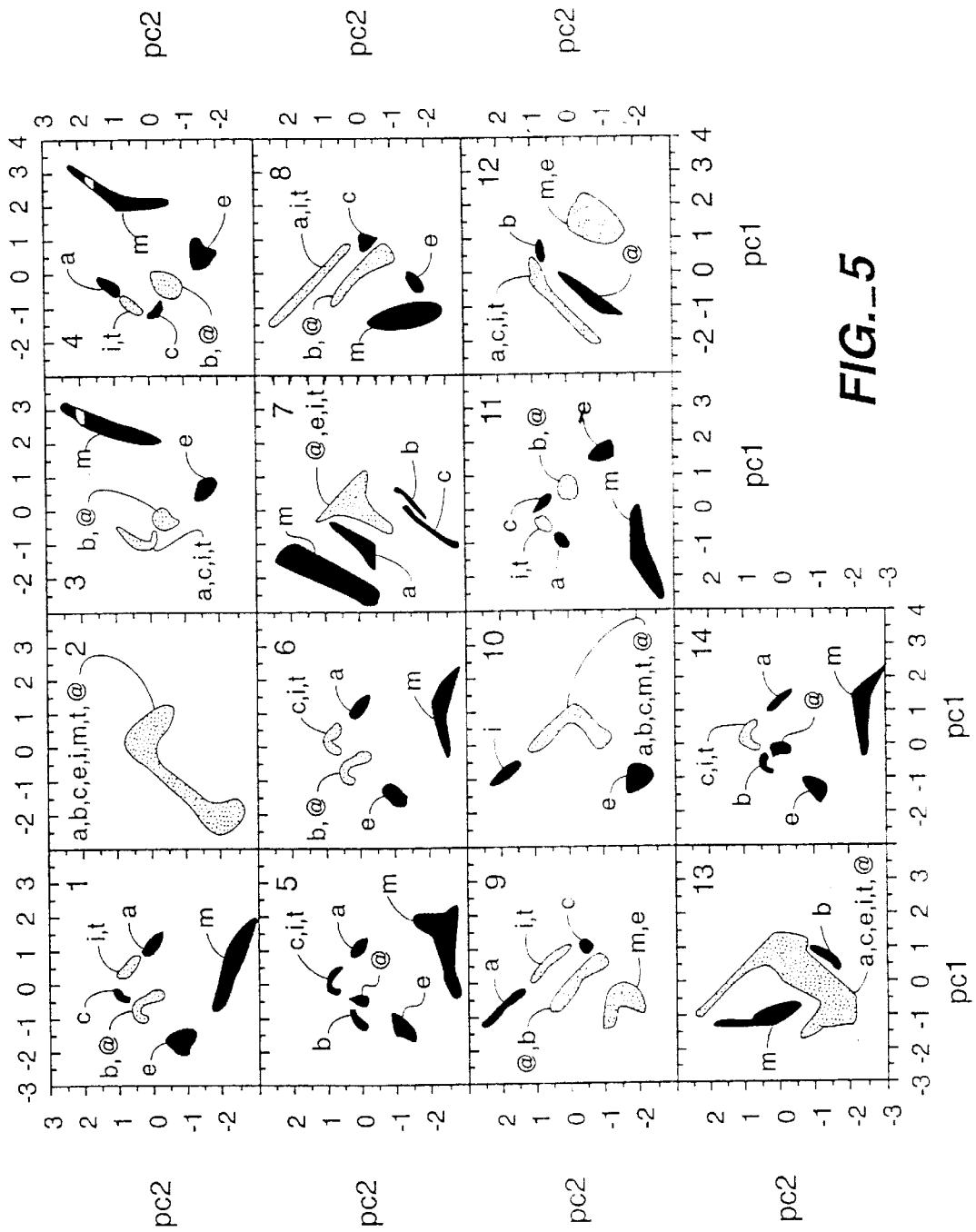
FIG._5

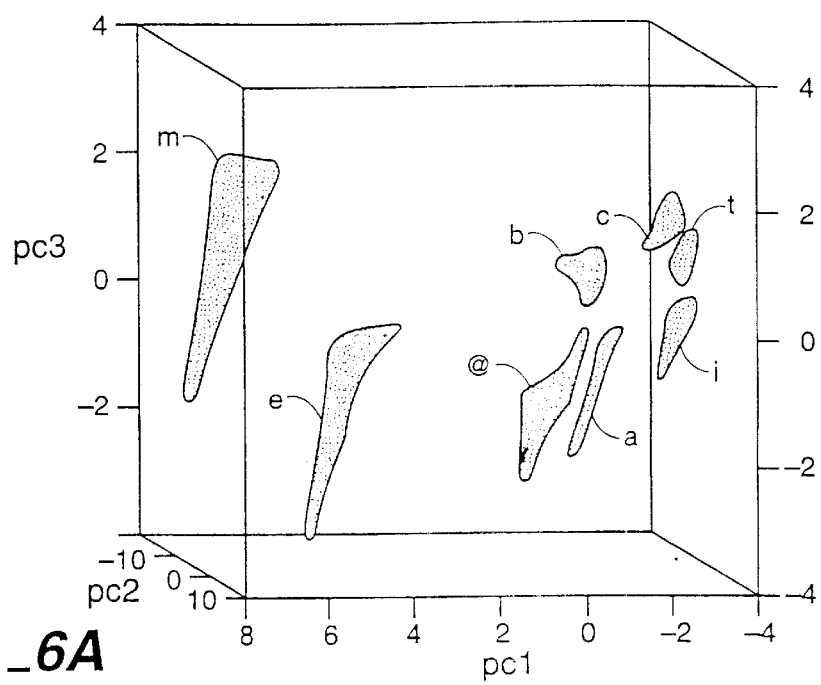
FIG._6A
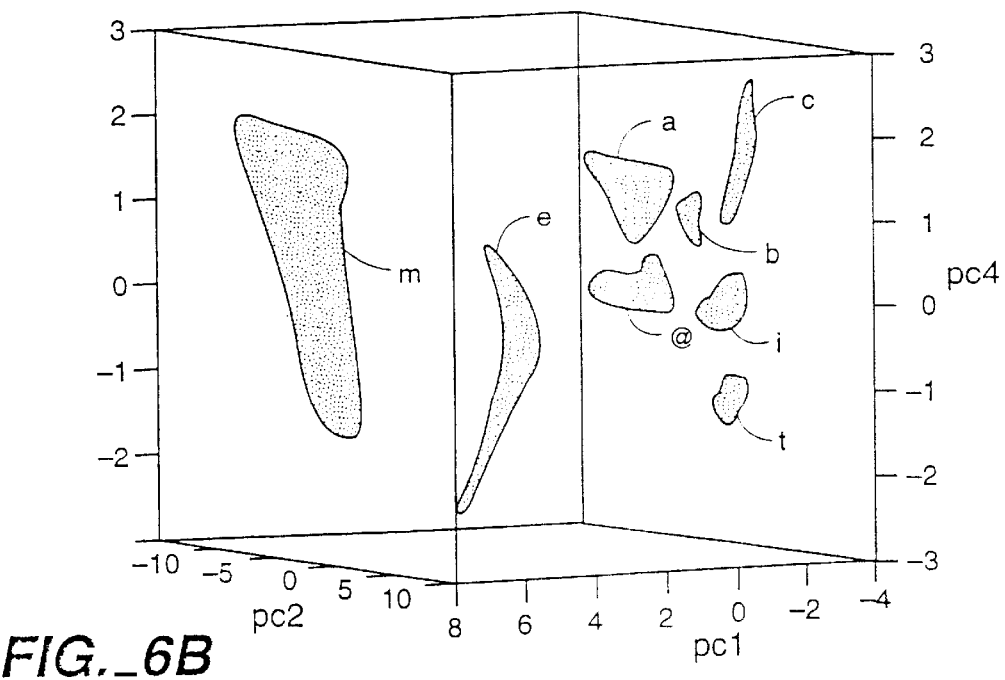
FIG._6B

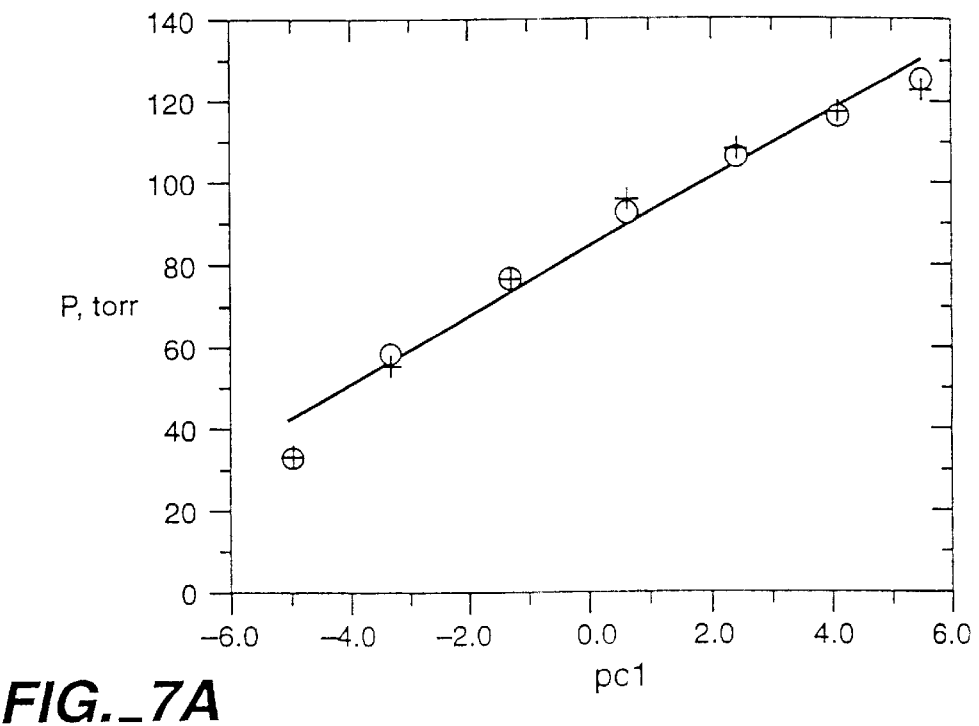
FIG._7A
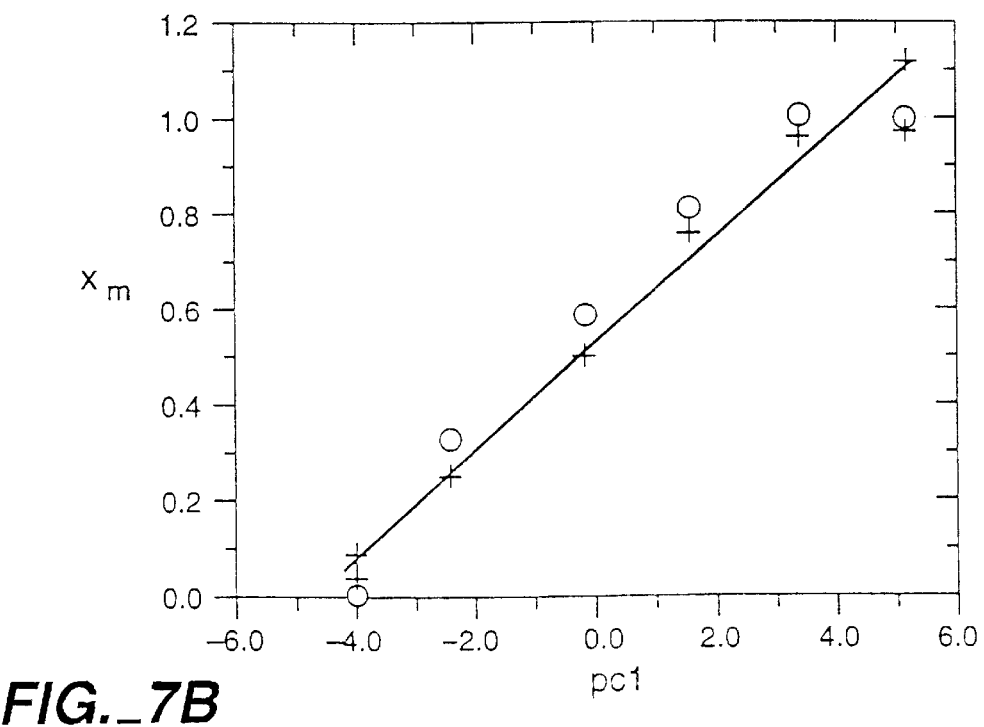
FIG._7B

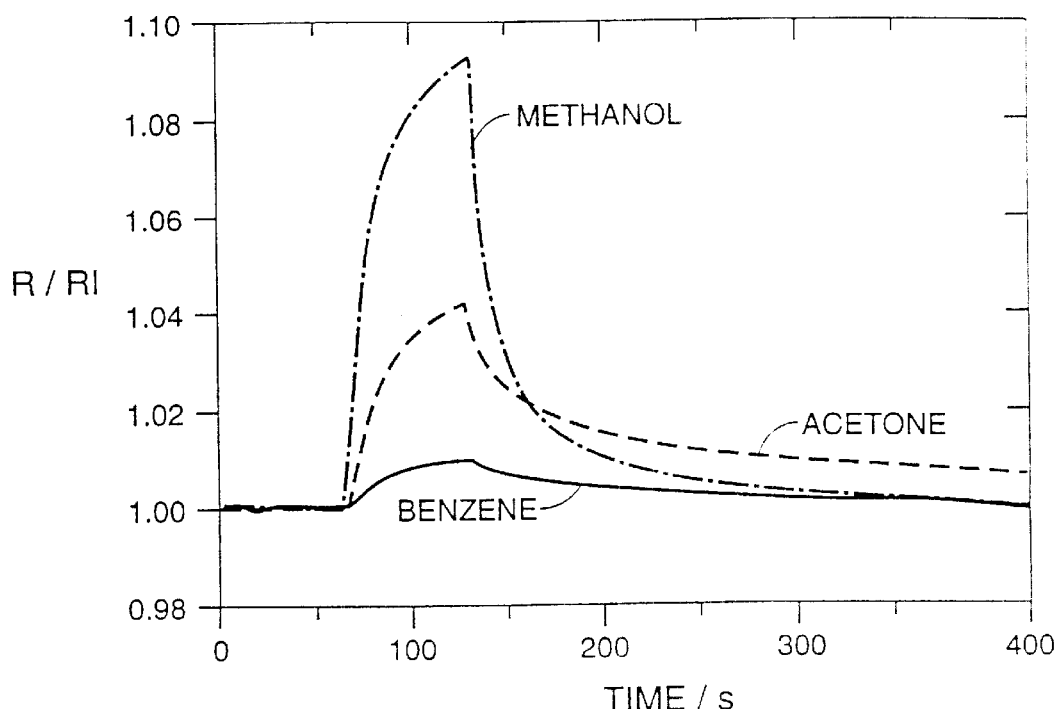
FIG._8
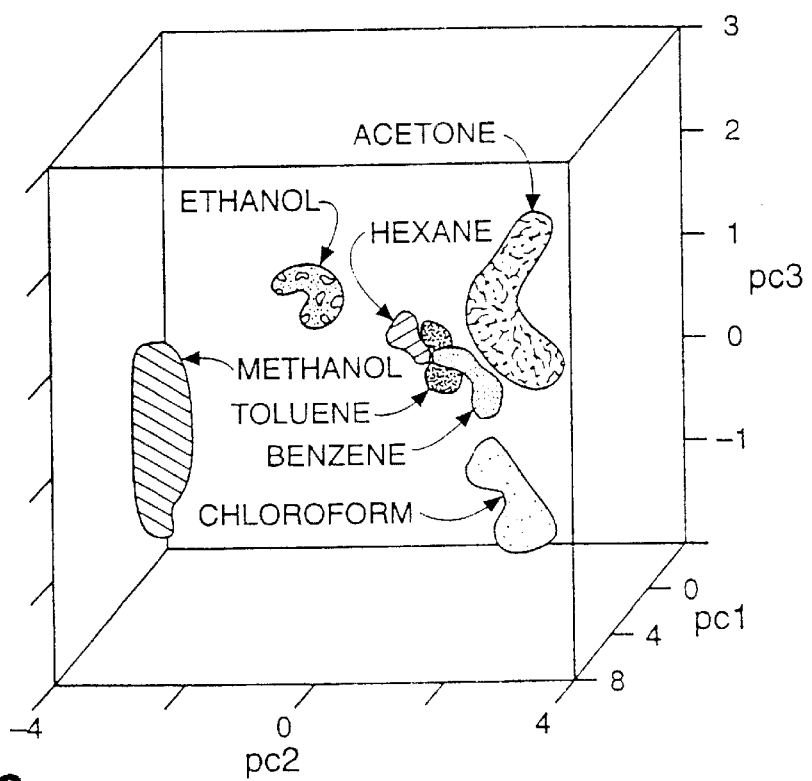
FIG._9

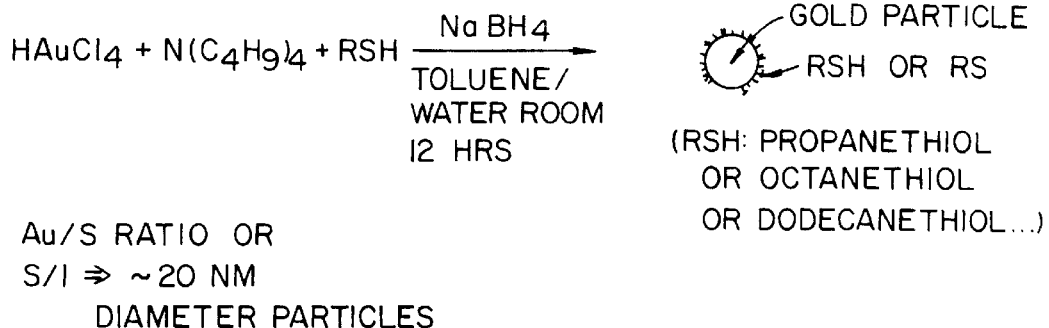
SONICATE MIXTURE, PLACE A DROP ON INTERDIGITATED ELECTRODE SUBSTRATE
SONICATE MIXTURE, PLACE A DROP ON INTERDIGITATED ELECTRODE SUBSTRATE
FIG. 10.

COLLOIDAL PARTICLES USED IN SENSING ARRAYS

RELATED APPLICATIONS

This application claims priority to and is a continuation-in-part of U.S. patent application Ser. No. 08/986,500, filed Jan. 4, 2000, now U.S. Pat. No. 6,010,616, which is a continuation of U.S. patent application Ser. No. 08/689,227, filed Dec. 16, 1997, now U.S. Pat. No. 5,698,089, which, in turn, is a continuation of U.S. patent application Ser. No. 08/410,809, filed Mar. 27, 1995, now U.S. Pat. No. 5,571,401. All applications are hereby expressly incorporated by reference in their entirety for all purposes. This application also claims priority to U.S. Provisional Patent Application Ser. No. 60/088,630, filed Jun. 9, 1998, and U.S. Provisional Patent Application Ser. No. 60/118,833, filed Feb. 5, 1999, both applications are hereby expressly incorporated by reference in their entirety for all purposes.

The research carried out in the subject application was supported in part by Grant No. DAAK60-97-K-9503 awarded by DARPA and Grant No. DAGSS-97-1-0187 awarded by ARO. The government may have certain rights on any patent issuing hereon.

FIELD OF INVENTION

This invention relates generally to sensors for detecting analytes in fluids. More particularly, it relates to an array of sensors useful for constructing "electronic noses" for analyzing complex vapors and producing a sample output.

BACKGROUND OF THE INVENTION

There is considerable interest in developing sensors that act as analogs of the mammalian olfactory system (1–2). This system is thought to utilize probabilistic repertoires of many different receptors to recognize a single odorant (3–4). In such a configuration, the burden of recognition is not on highly specific receptors, as in the traditional "lock-and-key" molecular recognition approach to chemical sensing, but lies instead on the distributed pattern processing of the olfactory bulb and the brain (5–6).

Prior attempts to produce a broadly responsive sensor array have exploited heated metal oxide thin film resistors (7–9), polymer sorption layers on the surfaces of acoustic wave resonators (10–11), arrays of electrochemical detectors (12–14), or conductive polymers (15–16). Arrays of metal oxide thin film resistors, typically based on $SnO_2$ films that have been coated with various catalysts, yield distinct, diagnostic responses for several vapors (7–9). However, due to the lack of understanding of catalyst function, $SnO_2$ arrays do not allow deliberate chemical control of the response of elements in the arrays nor reproducibility of response from array to array. Surface acoustic wave resonators are extremely sensitive to both mass and acoustic impedance changes of the coatings in array elements, but the signal transduction mechanism involves somewhat complicated electronics, requiring frequency measurement to 1 Hz while sustaining a 100 MHz Rayleigh wave in the crystal (10–11). Attempts have also been made to construct sensors with conducting polymer elements that have been grown electrochemically through nominally identical polymer films and coatings (15–18). Moreover, Pearce et al., (1993) Analyst 118:371–377, and Gardner et al., (1994) Sensors and Actuators B 18–19:240–243 describe, polypyrrole-based sensor arrays for monitoring beer flavor. Shurmer (1990) U.S. Pat. No. 4,907,441, describes general sensor arrays with particular electrical circuitry.

Although the foregoing systems have some usefulness, these still remains a need in the art for a low cost, broadly responsive analyte detection sensor array based on a variety of sensors. The present invention fulfills this and other needs.

SUMMARY OF THE INVENTION

The present invention relates to a device for detecting a chemical analyte in a fluid, which includes gases, vapors and liquids. As such, the present invention relates to a device for detecting a chemical analyte, comprising: a sensor array connected to a measuring apparatus having at least one sensor comprising regions of nonconductive material and conductive material compositionally different than the nonconductive material, wherein the conductive material comprises a nanoparticle; and a response path through the regions of nonconductive material and the conductive material. In certain aspects, the sensor array is based on a variety of "chemiresistor" elements. Such elements are simply prepared and are readily modified chemically to respond to a broad range of analytes. In addition, these sensors yield a rapid, low power signal in response to an analyte of interest, and their signals are readily integrated with software or hardware-based neural networks. The signal output can be in the form of resistance, impedance, capacitance, optics, fluorescence or other means useful for purposes of analyte identification.

In certain aspects, device includes a substrate having at least one surface and at least two sensors fabricated onto the surface, wherein each sensor has a first and second electrical lead which are electrically connected to a chemically sensitive resistor. The resistor comprises a plurality of alternating nonconductive regions (comprising a nonconductive organic material) and conductive regions (comprising a conductive material or particle). The electrical path between the first and second leads is transverse to (i.e., passes through) the plurality of alternating nonconductive and conductive regions. In use, the resistor provides a difference in resistance between the conductive elements when 1) contacted with a fluid comprising a chemical analyte at a first concentration, than when contacted with a fluid comprising the chemical analyte at a second different concentration or 2) contacted with a fluid comprising a first chemical analyte at a concentration, than when contacted with a fluid comprising a second chemical analyte (different from the first) at the same concentration.

The variability in chemical sensitivity from sensor to sensor is conveniently provided by qualitatively or quantitatively varying the composition of the conductive and/or nonconductive regions. For example, in one embodiment, the conductive material in each resistor is held constant (e.g., the same conductive material such as polypyrrole, or carbon black), while the nonconductive material varies between resistors (e.g., different polymers).

In another embodiment, the conductive material is a conductive particle, such as a nanoparticle. In certain embodiments, the alternating nonconductive regions can be a covalently attached ligand to a conductive core (the conductive region). These ligands can be polyhomo- or polyheterofunctionalized, thereby being suitable for the detection of various analytes. Arrays of such sensors are constructed with at least two sensors having different chemically sensitive resistors providing various differences in resistance. An electronic nose for detecting an analyte in a fluid can be constructed by using such arrays in conjunction with an electrical measuring device electrically connected to the conductive elements of each sensor. Such electronic noses can incorporate a variety of additional components, including means for monitoring the temporal response of each sensor, assembling and analyzing sensor data to determine analyte identity, analyte concentration, or quality control determinations. Methods of making and using the disclosed sensors, arrays and electronic noses are also provided.

BRIEF DESCRIPTION OF THE DRAWINGS

FIG. 1(A) shows an overview of sensor design; FIG. 1(B) shows an overview of sensor operation; and FIG. 1(C) shows an overview of system operation.

FIG. 2 shows a cyclic voltammogram of a poly(pyrrole)-coated platinum electrode. The electrolyte was 0.10 M $[(C_4H_9)_4N]^+[ClO_4]^-$ in acetonitrile, with a scan rat of 0.10 V $s^{-1}$.

FIG. 3(A) shows the optical spectrum of a spin coated poly(pyrrole) film that had been washed with methanol to remove excess pyrrole and reduced phosphomolybdic acid. FIG. 3(B) shows the optical spectrum of a spin-coated poly(pyrrole) film on indium-tin-oxide after 10 potential cycles between +0.70 and −1.00 V vs. SCE (Saturated Calomel Reference Electrode) in 0.10 M $[(C_4H_9)_4N]^+$ $[ClO_4]^-$ in acetonitrile at a scan rate of 0.10 V $-s^{-1}$. The spectra were obtained in 0.10 M $KCl-H_2O$.

FIG. 4(A) shows a schematic of a sensor array showing an enlargement of one of the modified ceramic capacitors used as sensing elements. The response patterns to various analytes generated by the sensor array described in Table 5 are displayed for acetone FIG. 4(B); benzene FIG. 4(C); and ethanol FIG. 4(D).

FIG. 5. Principle component analysis of autoscaled data from individual sensors containing different plasticizers. The numbers in the upper right hand corner of each square refer to the different sensor elements described in Table 5.

FIGS. 6(A) and 6(B) shows the principle component analysis of data obtained from all sensors described in Table 5. Conditions and symbols are identical to FIGS. 5(A)–5(D). FIG. 6A shows data represented in the first three principle components pc1, pc2 and pc3, while FIG. 6B shows the data when represented in pc1, pc2, and pc4. A higher degree of discrimination between some solvents could be obtained by considering the fourth principle component as illustrated by larger separations between chloroform, tetrahydrofuran, and isopropyl alcohol in FIG. 6B.

FIG. 7(A) shows the plot of acetone partial pressure (O) as a function of the first principle component; linear least square fit (−) between the partial pressure of acetone and the first principle component ($P_a$=8.26·pc1+83.4, $R^2$=0.989); acetone partial pressure (+) predicted from a multi-linear least square fit between the partial pressure of acetone and the first three principle components ($P_a$=8.26·pc1−0.673·pc2+6.25·pc3+83.4, $R^2$=0.998). FIG. 7(B) shows the plot of the mole fraction of methanol, $x_m$, (O) in a methanol-ethanol mixture as a function of the first principle component; linear least square fit (−) between xm and the first principle component (xm=0.112·pc1+0.524, $R^2$=0.979); $x_m$ predicted from a multi-linear least square fit (+) between $X_m$ and the first three principle components ($x_m$=0.112·pc1−0.0300·pc2−0.0444·pc3+0.524, $R^2$=0.987).

FIG. 8 shows the resistance response of a poly(N-vinylpyrrolidone):carbon black (20 w/w % carbon black) sensor element to methanol, acetone, and benzene. The analyte was introduced at t=60 s for 60 s. Each trace is normalized by the resistance of the sensor element (approx. 125Ω) before each exposure.

FIG. 9 shows the first three principal components for the response of a carbon-black based sensor array with 10 elements. The non-conductive components of the composites used are listed in Table 5, and the resistors were 20 w/w % carbon black.

FIGS. 10(A)–(B) shows a synthetic scheme of various nanoparticles of the present invention.

DETAILED DESCRIPTION OF THE INVENTION

Figure 11A:
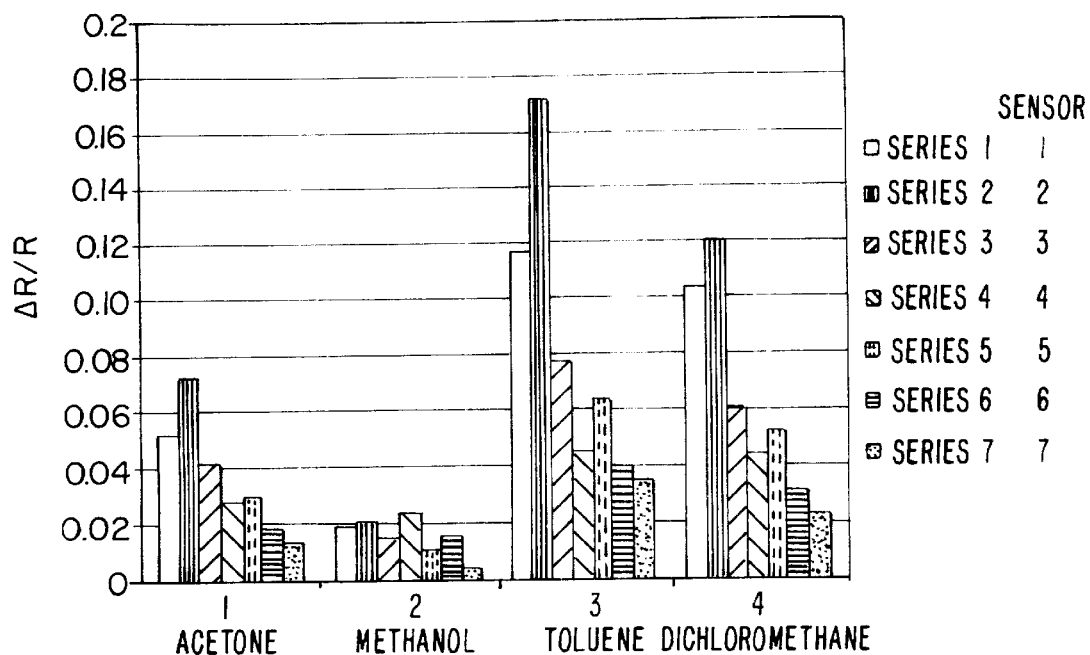
FIGS. 11(A)–(B) shows response patterns of various sensors in an array to different analytes.

The present invention provides sensor arrays for detecting an analyte in a fluid, which may be gaseous or liquid in nature in conjunction with an electrical measuring apparatus. These arrays comprise a plurality of compositionally different chemical sensors. In certain embodiments, the present invention relates to a device for detecting a chemical analyte comprising: a sensor array connected to a measuring apparatus having at least one sensor comprising regions of nonconductive material and conductive material compositionally different than the nonconductive material, wherein the conductive material comprises a nanoparticle; and a response path through the regions of nonconductive material and the conductive material.

In certain aspects, the sensor array is based on a variety of "chemiresistor" elements. Each sensor comprises at least first and second conductive leads electrically coupled to and separated by a chemically sensitive resistor. The leads may be any convenient conductive material, usually a metal, and may be interdigitated to manipulate the circuit resistance and maximize the signal to noise ratio.

The resistor comprises a plurality of alternating nonconductive and conductive regions transverse to the electrical path between the conductive leads. Generally, the resistors are fabricated by blending a conductive material with a nonconductive material, e.g., an organic polymer, such that the electrically conductive path between the leads coupled to the resistor is interrupted by gaps of non-conductive organic polymer material. For example, in a colloid, suspension or dispersion of particulate conductive material in a matrix of nonconductive organic polymer material, the matrix regions separating the particles provide the gaps. In certain embodiments, the colloid is a nanoparticle that is optionally stabilized. The nonconductive gaps range in path length from about 10 to 1,000 angstroms, usually on the order of 100 angstroms, providing individual resistance of about 10 to 1,000 mΩ, usually on the order of 100 mΩ, across each gap. The path length and resistance of a given gap is not constant, but rather is believed to change as the nonconductive organic polymer of the region absorbs, adsorbs or imbibes an analyte. Accordingly, the dynamic aggregate resistance provided by these gaps in a given resistor is a linear or non-linear function of analyte permeation of the nonconductive regions. In some embodiments, the conductive material may also contribute to the dynamic aggregate resistance as a linear or nonlinear function of analyte permeation (e.g., when the conductive material is a conductive organic polymer, such as polypyrrole).

In some embodiments, the resistor comprises a plurality of alternating regions of a conductor with regions of an insulator. Without being bound to any particular theory, it is believed that the electrical pathway that an electrical charge traverses between the two contacting electrodes traverses both the region of a conductor and the region of an insulator. In this embodiment, the conducting region can be anything that can carry electrons from atom to atom, including, but not limited to, a material, a particle, a metal, a polymer, a substrate, an ion, an alloy, an organic material, (e.g., carbon, graphite, etc.) an inorganic material, a biomaterial, a solid, a liquid, a gas or mixtures thereof.

The insulating region (i.e., non-conductive region) can be anything that can impede electron flow from atom to atom, including, but not limited to, a material, a polymer, a plasticizer, an organic material, an organic polymer, a filler, a ligand, an inorganic material, a biomaterial, a solid, a liquid, a gas and mixtures thereof.

A wide variety of conductive materials and nonconductive organic polymer materials can be used. Table 1 provides exemplary conductive materials for use in resistor fabrication; mixtures, such as those listed, can also be used. Table 2 provides exemplary nonconductive organic polymer materials; blends and copolymers, such as the polymers listed here, can also be used. Combinations, concentrations, blend stoichiometries, percolation thresholds, etc. are readily determined empirically by fabricating and screening prototype resistors (chemiresistors) as described below.

TABLE 1

| Major Class | Examples |
|---|---|
| Organic Conductors | conducting polymers (poly(anilines), poly(thiophenes), poly(pyrroles), poly(acetylenes), etc.)), carbonaceous materials (carbon blacks, graphite, coke, $C_{60}$, etc.), charge transfer complexes (tetramethylparaphenylenediamine-chloranile, alkali metal tetracyanoquinodimethane complexes, tetrathiofulvalene halide complexes, etc.), etc. |
| Inorganic Conductors | metals and metal alloys (Ag, Au, Cu, Pt, AuCu alloy, etc.), highly doped semiconductors (Si, GaAs, InP, $MoS_2$, $TiO_2$, etc.), conductive metal oxides ($In_2O_3$, $SnO_2$, $Na_xPt_3O_4$, etc.), superconductors ($YBa_2Cu_3O_7$, $Tl_2Ba_2Ca_2Cu_3O_{10}$, etc.), etc. |
| Mixed inorganic/ organic Conductors | Tetracyanoplatinate complexes, Iridium halocarbonyl complexes, stacked macrocyclic complexes, etc. |

TABLE 2

| Major Class | Examples |
|---|---|
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitriles), poly(vinyl esters), poly(styrenes), poly(arylenes), etc. |
| Main-chain acyclic heteroatom polymers | poly(oxides), poly(carbonates), poly(esters), poly(anhydrides), poly(urethanes), poly(sulfonates), poly(siloxanes), poly(sulfides), poly(thioesters), poly(sulfones), poly(sulfonamides), poly(amides), poly(ureas), poly(phosphazenes), poly(silanes), poly(silazanes), etc. |
| Main-chain heterocyclic polymers | poly(furan tetracarboxylic acid diimides), poly(benzoxazoles), poly(oxadiazoles), poly(benzothiazinophenothiazines), poly(benzothiazoles), poly(pyrazinoquinoxalines), poly(pyromellitimides), poly(quinoxalines), poly(benzimidazoles), poly(oxindoles), poly(oxoisoindolines), poly(dioxoisoindolines), poly(triazines), poly(pyridazines), poly(piperazines), poly(pyridines), poly(piperidines), poly(triazoles), poly(pyrazoles), poly(pyrrolidines), poly(carboranes), poly(oxabicyclononanes), poly(dibenzofurans), poly(phthalides), poly(acetals), poly(anhydrides), carbohydrates, etc |

In certain other embodiments, the conductive material is a conductive particle, such as a colloidal nanoparticle. As used herein the term "nanoparticle" refers to a conductive cluster, such as a metal cluster, having a diameter on the nanometer scale. As described more fully below, such nanoparticles are optionally stabilized with organic ligands.

Examples of colloidal nanoparticles for use in accordance with the present invention are described in the literature (32–38). In this embodiment, the nonconductive region can optionally be a ligand that is attached to a central core making up the nanoparticle. These ligands i.e., caps, can be polyhomo or polyheterofunctionalized, thereby being suitable for detecting a variety of chemical analytes. The nanoparticles, i.e., clusters, are stabilized by the attached ligands. As explained more fully below, by varying the concentration of the synthetic reagents, the particle size can be manipulated and controlled.

In certain embodiments, the resistors are nanoparticles comprising a central core conducting element and an insulating attached ligand optionally in a polymer matrix. With reference to Table 1, various conducting materials are suitable for the central core. In certain preferred embodiments, the nanoparticles have a metal core. Preferred metal cores include, but are not limited to, Au, Ag, Pt, Pd, Cu, Ni, AuCu and mixtures thereof Gold (Au) is especially preferred. These metallic nanoparticles can be synthesized using a variety of methods. In a preferred method of synthesis, a modification of the protocol developed by Brust et al. (30) (the teachings of which are incorporated herein by reference), can be used. Using alkanethiolate gold clusters as an illustrative example, and not in any way to be construed as limiting, the starting molar ratio of $HAuCl_4$ to alkanethiol is selected to construct particles of the desired diameter. The organic phase reduction of $HAuCl_4$ by an alkanethiol and sodium borohydride leads to stable, modestly polydisperse, alkanethiolate-protected gold clusters having a core dimension of about 1 nm to about 100 nm. Preferably, the nanoparticles range in size from about 1 nm to about 50 nm. More preferably, the nanoparticles range in size from about 5 nm to about 20 nm.

In this reaction, a molar ratio of $HAuCl_4$ to alkanethiol of greater than 1:1 leads to smaller particle sizes, whereas a molar ratio of $HAuCl_4$ to alkanethiol less than 1:1 yield clusters which are larger in size. Thus, by varying the ratio of $HAuCl_4$ to alkanethiol, it is possible to generate various sizes and dimensions of nanoparticles suitable for a variety of analytes. Although not intending to be bound by any particular theory, it is believed that during the chemical reaction, as neutral gold particles begin to nucleate and grow, the size of the central core is retarded by the ligand monolayer in a controlled fashion. Using this reaction, it is then possible to generate nanoparticles of exacting sizes and dimensions.

Ligands or caps of various chemical classes are suitable for use in the present invention. Ligands include, but are not limited to, alkanethiols having alkyl chain lengths of about $C_1$–$C_{30}$. In a preferred embodiment, the alkyl chain lengths of the alkanethiols are between about $C_3$ to about $C_{12}$. In this embodiment, it is noted that the nanoparticles' conductivity decreases as alkane length increases.

Alkanethiols suitable for use can also be polyhomofunctionalized or polyheterofunctionalized (such as, at the ω-position, or last position of the chain). As used herein, the term "polyhomofunctionalized" means that the same chemical moiety has been used to modify the ligand at various positions within the ligand. Chemical moieties suitable for functional modification include, but are not limited to, bromo, chloro, iodo, fluoro, amino, hydroxyl, thio, phosphino, alkylthio, cyano, nitro, amido, carboxyl, aryl, heterocyclyl, ferrocenyl or heteroaryl. The ligands can be attached to the central core by various methods including, but not limited to, covalent attachment, and electrostatic attachment. As used herein, the term "polyheterofunctionalized" means that different chemical moieties or functional groups are used to modify the ligands at various positions.

It is possible to synthesize polyheterofunctionalized clusters via place exchange reactions (34). This reaction can be a simultaneous exchange of a mixture of thiols onto the nanoparticle, or alternatively, a stepwise progressive exchange of different thiols, isolating the nanoparticle product after each step. The place exchange reaction replaces an existing alkanethiol with an alkanethiol comprising a functional group.

In addition to alkanethiols, various suitable ligands include, but are not limited to, polymers, such as polyethylene glycol; surfactants, detergents, biomolecules, such as polysaccharides: protein complexes, polypeptides, dendrimeric materials, oligonucleotides, fluorescent moieties and radioactive groups.

In certain embodiments, the core, such as a metal core, acts as a scaffolding, which can support more complex organic ligands. These scaffolding can be used as a solid support for combinatorial synthesis. In this embodiment, various functional groups can be attached to the core to achieve structural diversity. Optionally, the combinatorial synthesis can be performed using a robotic armature system. In general, these systems include automated workstations like the automated apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual operations performed by a synthetic chemist. The nature and implementation of modifications to these methods (if any) so that they can operate will be apparent to persons skilled in the relevant art.

It is possible that steric crowding can accompany the introduction of numerous functional groups onto the surface of the nanoparticle core that is occupied by the ligand, such as an alkanethiolate ligand. The number of ligands and the amount of functionalization is directly proportional to the size of the central core. In practice, electrical conductivity becomes more difficult to measure when the ratio of metal to ligand decreases. Conversely, as the ratio of metal to ligand increases, the core can become too big to allow the ligands to solubilize the particle. Thus, those of skill in the art will select suitable ratios of core size to ligand amount for particular uses.

In certain other embodiments, sensors are prepared as composites of "naked" nanoparticles and an insulating material is added. As used herein, the term "naked nanoparticles" means that the core has no covalently attached ligands or caps. A wide variety of insulating materials can be used in this embodiment. Preferred insulating materials are organic polymers. Suitable organic polymers include, but are not limited to, polycaprolactone, polystyrene, and poly(methyl methacrylate). Varying the insulating material types, concentration, size, etc., provides the diversity necessary for an array of sensors. In one embodiment, the metal to insulating polymer ratio is about 50% to about 90% (wt/wt). Preferably, the metal to insulating polymer ratio is about 85% to about 90% (wt/wt).

Sensors can also be prepared using the nanoparticle and an alkylthiol ligand as the sole insulating matrix. In this embodiment, varying the ligand, ligand size and functionalization can provide sensor diversity. Sensor films can be cast on interdigitated electrode substrates. Sensors that are comprised either of naked nanoparticles or nanoparticles having ligands show a reversible increase in electrical resistance upon exposure to chemical vapors. Moreover, it has been shown that as the length of the ligand chain increases, the conductivity of the resistors decreases.

Nanoparticles, such as alkylthiol-capped gold colloids, are soluble or dispersible in a wide range of organic solvents having a large spectrum of polarity. This diverse solubility permits a good selection of co-soluble insulating materials. Alternative capping agents, which include amines and phosphines, can extend the use to virtually any solvent. Simultaneous variation of ligand and insulating material, such as organic polymers, can provide great diversity in multidimensional sensor arrays.

Without intending to be bound by any particular theory, it is believed that the chemical analyte diffuses into and is dispersed within the nanoparticle ligands or insulating material and thereby changes the electrical properties of the sensors. These property changes which are then detected include, but are not limited to, resistance, capacitance, conductivity, magnetism, optical changes and impedance.

In certain embodiments, the sensor arrays of the present invention comprise other sensor types. Various sensors suitable for detection of analytes include, but are not limited to: surface acoustic wave (SAW) sensors; quartz microbalance sensors; conductive composites; chemiresitors; metal oxide gas sensors, such as tin oxide gas sensors; organic gas sensors; metal oxide field effect transistor (MOSFET); piezoelectric devices; infrared sensors; sintered metal oxide sensors; Pd-gate MOSFET; metal FET structures; metal oxide sensors, such as a Tuguchi gas sensors; phthalocyanine sensors; electrochemical cells; conducting polymer sensors; catalytic gas sensors; organic semiconducting gas sensors; solid electrolyte gas sensors; piezoelectric quartz crystal sensors; dye-impregnated polymer films on fiber optic detectors; polymer-coated micromirrors; electrochemical gas detectors; chemically sensitive field-effect transistors; carbon black-polymer composite chemiresistors; micro-electro-mechanical system devices; and micro-opto-electro-mechanical system devices and Langmuir-Blodgett film sensors. In other embodiments, these foregoing sensor types comprise nanoparticles of the present invention.

The chemiresistors of the present invention can be fabricated by many techniques including, but not limited to, solution casting, suspension casting and mechanical mixing. In general, solution casting routes are advantageous because they provide homogeneous structures and are easy to process. With solution casting routes, resistor elements can be easily fabricated by spin, spray or dip coating. Since all elements of the resistor must be soluble, however, solution casting routes are somewhat limited in their applicability. Suspension casting still provides the possibility of spin, spray or dip coating, but more heterogeneous structures than with solution casting are expected. With mechanical mixing, there are no solubility restrictions since it involves only the physical mixing of the resistor components, but device fabrication is more difficult since spin, spray and dip coating are no longer possible. A more detailed discussion of each of these follows.

For systems where both the conducting and non-conducting media or their reaction precursors are soluble in a common solvent, the chemiresistors can be fabricated by solution casting. The oxidation of pyrrole by phosphomolybdic acid presented herein represents such a system. In this reaction, the phosphomolybdic acid and pyrrole are dissolved in tetrahydrofuran (THF) and polymerization occurs upon solvent evaporation. This allows for THF soluble non-conductive polymers to be dissolved into this reaction mixture, thereby allowing the blend to be formed in a single step upon solvent evaporation. The choice of non-conductive polymers in this route is, of course, limited to those that are soluble in the reaction media. For the poly (pyrrole) case described above, preliminary reactions were performed in THF, but this reaction should be generalizable to other non-aqueous solvent such as acetonitrile or ether. A variety of permutations on this scheme are possible for other conducting polymers. Some of these are listed below. Certain conducting polymers, such as substituted poly (cyclooctatetraenes), are soluble in their undoped, non-conducting state in solvents such as THF or acetonitrile. Consequently, the blends between the undoped polymer and polymer containing other organic materials can be formed from solution casting. After which, the doping procedure (exposure to $I_2$ vapor, for instance) can be performed on the blend to render the substituted poly(cyclooctatetraene) conductive. Again, the choice of non-conductive polymers is limited to those that are soluble in the solvents that the undoped conducting polymer is soluble in and to those stable to the doping reaction. Certain conducting polymers can also be synthesized via a soluble precursor polymer. In these cases, blends between the precursor polymer and the non-conducting polymer can first be formed followed by chemical reaction to convert the precursor polymer into the desired conducting polymer. For instance, poly(p-phenylene vinylene) can be synthesized through a soluble sulfonium precursor. Blends between this sulfonium precursor and the non-conductive polymer can be formed by solution casting. After which, the blend can be subjected to thermal treatment under vacuum to convert the sulfonium precursor into the desired poly(p-phenylene vinylene).

In suspension casting, one or more of the components of the resistor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the non-conductive polymer is dissolved in an appropriate solvent (such as THF, acetonitrile, water, etc.). Colloidal silver is then suspended in this solution and the resulting mixture is used to dip coat electrodes.

Mechanical mixing is suitable for all of the conductive/non-conductive combinations possible. In this technique, the materials are physically mixed in a ball-mill or other mixing device. For instance, carbon black/non-conductive polymer composites are readily made by ball-milling. When the non-conductive polymer can be melted or significantly softened without decomposition, mechanical mixing at elevated temperatures can improve the mixing process. Alternatively, composite fabrication can sometimes be improved by several sequential heat and mix steps.

For the nanoparticles with and without ligands, spray deposition can be used. In this method, the temperature can be elevated to promote a uniform film formation. The stable dispersions and homogenous films of these nanoparticles can also facilitate reproducible fabrication of the vapor sensors.

Once fabricated, the individual elements can be optimized for a particular application by varying their chemical make up and morphologies. The chemical nature of the resistors determines to which analytes they will respond and their ability to distinguish different analytes. The relative ratio of conductive to insulating components determines the magnitude of the response since the resistance of the elements becomes more sensitive to sorbed molecules as the percolation threshold is approached. The film morphology is also important in determining response characteristics. For instance, thin films respond more quickly to analytes than do thick ones. Hence, with an empirical catalogue of information on chemically diverse sensors made with varying ratios of insulating to conducting components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

The resistor may itself form a substrate for attaching the lead or the resistor. For example, the structural rigidity of the resistors may be enhanced through a variety of techniques: chemical or radiation cross-linking of polymer components (dicumyl peroxide radical cross-linking, UV-radiation cross-linking of poly(olefins), sulfur cross-linking of rubbers, e-beam cross-linking of Nylon, etc.), the incorporation of polymers or other materials into the resistors to enhance physical properties (for instance, the incorporation of a high molecular weight, high transition metal (Tm) polymers), the incorporation of the resistor elements into supporting matrices, such as clays or polymer networks (forming the resistor blends within poly(methylmethacrylate) networks or within the lamellae of montmorillonite, for instance), etc. In another embodiment, the resistor is deposited as a surface layer on a solid matrix that provides means for supporting the leads. Typically, the solid matrix is a chemically inert, non-conductive substrate, such as a glass or ceramic.

Sensor arrays particularly well-suited to scaled up production are fabricated using integrated circuit (IC) design technologies. For example, the chemiresistors can easily be integrated onto the front end of a simple amplifier interfaced to an A/D converter to efficiently feed the data stream directly into a neural network software or hardware analysis section. Micro-fabrication techniques can integrate the chemiresistors directly onto a micro-chip which contains the circuitry for analogue signal conditioning/processing and then data analysis. This provides for the production of millions of incrementally different sensor elements in a single manufacturing step using ink-jet technology. Controlled compositional gradients in the chemiresistor elements of a sensor array can be induced in a method analogous to how a color ink-jet printer deposits and mixes multiple colors. However, in this case rather than multiple colors, a plurality of different polymers in solution which can be deposited are used. A sensor array of a million distinct elements only requires a 1 cm×1 cm sized chip employing lithography at the 10 $\mu$m feature level, which is within the capacity of conventional commercial processing and deposition methods. This technology permits the production of sensitive, small-sized, stand-alone chemical sensors.

Preferred sensor arrays have a predetermined inter-sensor variation in the structure or composition of the nonconductive organic polymer regions. The variation may be quantitative and/or qualitative. For example, the concentration of the nonconductive organic polymer in the blend can be varied across sensors. Alternatively, a variety of different organic polymers may be used in different sensors.

In certain embodiments, a variety of capped colloids can be used as different sensors. Optionally, a capped colloid system can be used in conjunction with a variety of polymer matrices as different sensors. An electronic nose for detecting an analyte in a fluid is fabricated by electrically coupling the sensor leads of an array of compositionally different sensors to an electrical measuring device. The device measures changes in resistivity at each sensor of the array, preferably simultaneously and preferably over time. Frequently, the device includes signal processing means and is used in conjunction with a computer and data structure for comparing a given response profile to a structure-response profile database for qualitative and quantitative analysis. Typically, such a nose comprises at least ten, usually at least 100, and often at least 1000 different sensors, though with mass deposition fabrication techniques described herein or otherwise known in the art, arrays of on the order of at least $10^6$ sensors are readily produced.

In operation, each resistor provides a first electrical resistance between its conductive leads when the resistor is contacted with a first fluid comprising a chemical analyte at a first concentration, and a second electrical resistance between its conductive leads when the resistor is contacted with a second fluid comprising the same chemical analyte at a second different concentration. The fluids may be liquid or gaseous in nature. The first and second fluids may reflect samples from two different environments, a change in the concentration of an analyte in a fluid sampled at two time points, a sample and a negative control, etc. The sensor array necessarily comprises sensors which respond differently to a change in an analyte concentration, i.e., the difference between the first and second electrical resistance of one sensor is different from the difference between the first and second electrical resistance of another sensor.

In a preferred embodiment, the temporal response of each sensor (resistance as a function of time) is recorded. The temporal response of each sensor may be normalized to a maximum percent increase and percent decrease in resistance which produces a response pattern associated with the exposure of the analyte. By iterative profiling of known analytes, a structure-function database correlating analytes and response profiles is generated. Unknown analyte may then be characterized or identified using response pattern comparison and recognition algorithms. Accordingly, analyte detection systems comprising sensor arrays, an electrical measuring device for detecting resistance across each chemiresistor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

A wide variety of analytes and fluids may be analyzed by the disclosed sensors, arrays and noses so long as the subject analyte is capable of generating a differential response across a plurality of sensors of the array. Analyte applications include broad ranges of chemical classes including, but not limited to organics such as alkanes, alkenes, alkynes, dienes, alicyclic hydrocarbons, arenes, alcohols, ethers, ketones, aldehydes, carbonyls, carbanions, polynuclear aromatics and derivatives of such organics, e.g., halide derivatives, etc., biomolecules such as sugars, isoprenes and isoprenoids, fatty acids and derivatives, etc. Accordingly, commercial applications of the sensors, arrays and noses include environmental toxicology and remediation, biomedicine, materials quality control, food and agricultural products monitoring, etc.

The general method for using the disclosed sensors, arrays and electronic noses, for detecting the presence of an analyte in a fluid involves resistively sensing the presence of an analyte in a fluid with a chemical sensor comprising first and second conductive leads electrically coupled to and separated by a chemically sensitive resistor as described above by measuring a first resistance between the conductive leads when the resistor is contacted with a first fluid comprising an analyte at a first concentration and a second different resistance when the resistor is contacted with a second fluid comprising the analyte at a second different concentration.

The following examples are offered by way of illustration and not by way of limitation.

EXAMPLES

Example 1

This example illustrates the synthesis of colloidal gold nanoparticles with covalently attached alkylthiol ligands.

The gold nanoparticles described herein were prepared using a procedure similar to the protocol developed by Brust et al. All solutions were prepared using volumetric procedures. Into a 100 ml flask, $HAuCl_4$ (0.3047 mmol) and tetraoctyl-ammonium bromide (0.6764 mmol) were added. A yellow solution was formed which immediately turned brown. The mixture was shaken and, while stirring, 1-dodecanethiol (0.08684 mmol) was added followed by sodium borohydride (3.352 mmol). After about 12 hours, the organic layer was separated and left an interphase layer. The aqueous layer was extracted a second time with hexane, which again left an interphase layer. The organic layer was evaporated in vacuo to about 5 mL and about 200 ml of absolute ethanol was added. The solution was stirred at $-78°$ C. for 4 hours and 30 ml of water was added until a precipitate appeared. Afterwards, the precipitated product was collected and washed with cold ethanol. The solution was concentrated under vacuum, but without rotation. The dried product (20.3 mg) was confirmed by UV-Vis spectroscopic analysis.

Example 2

This example illustrates conductivity measurements using the gold nanoparticles made in accordance with Example 1.

Conductivity measurements were recorded using ceramic capacitors (K5M 224) 22 nF, approximately 2×4×4 mm in size from Kemet Electronics. Four capacitors were prepared as described in *Chem. Mater.* Vol. 8, 1996, with the following modifications. The capacitors were ground off with a dremel tool. Next, the capacitors were sanded and polished. Finally the capacitors were sonicated.

The capacitors were coated with a toluene solution of gold nanoparticles from Example 1 and their resistance was measured. The capacitors had approximately 0.5 MΩ resistance.

Example 3

This example illustrates the use of gold nanoparticles as the conductive element in vapor sensors. Studies focused on the fabrication and application of nanoscale gold conductors in polymer composite sensors.

The conductors were prepared with a modified procedure of Hostetler et al. (33). Briefly, short alkyl chain thiols were used as the passivating agent in conductor fabrication. Pentanethiol and hexanethiol capped particles, although soluble, generally have high electrical resistance. Propanethiol passivated gold nanoparticles formed highly conductive, but less soluble, aggregates during the purification procedure when a ratio of 6:1 gold:thiol was used. This passivated gold material was used as the conductor region. An array of 17 sensors was constructed using various organic polymers as the insulating region (see, Table 3), along with the propyl cap region.

Figure 11B:
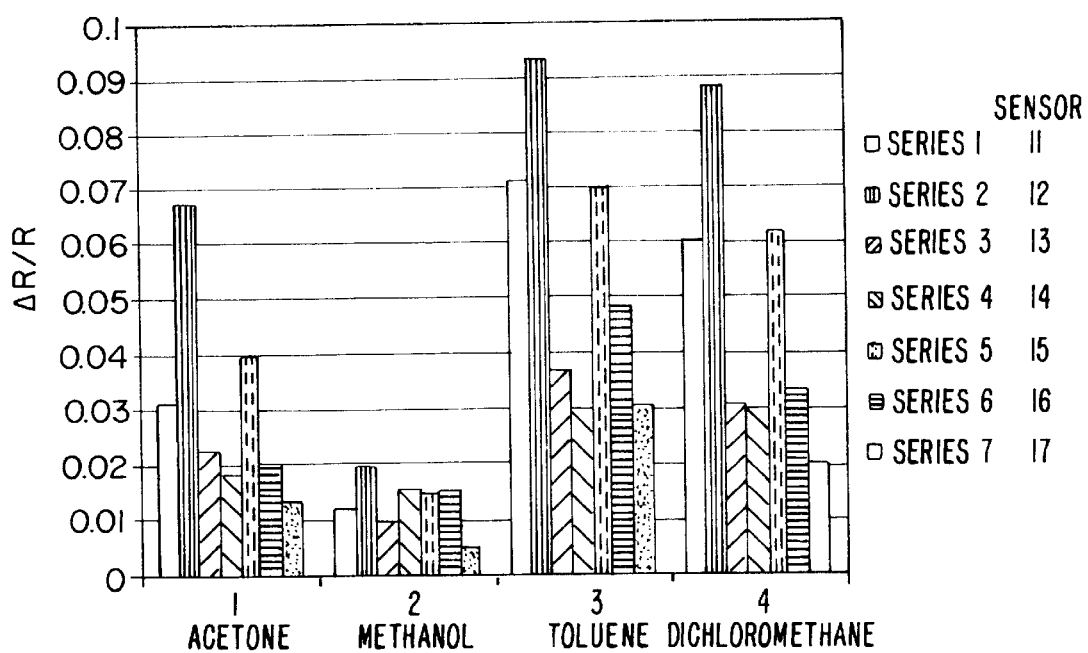

With reference to FIG. 11, exposure response patterns of the composite sensors to diluted vapor from polar and nonpolar solvents are illustrated. The results indicated that in general, sensors containing more polar polymers respond more to polar analytes and sensors containing nonpolar polymers respond more to nonpolar analytes. Additional exposure data obtained with these composite sensors with other analytes was also obtained. (data not shown).

TABLE 3

|  | g/mole | Mass (g) | moles | Equiv. | Target (g) | Density (g/mL) | Target (µL) | Solvent (mL) |
|---|---|---|---|---|---|---|---|---|
| $HAuC_{14}$ | 393.83 | 0.6425 | 1.63E-03 | 1 | | | | 25 |
| $N(C_8H_{17})_4Br$ | 546.82 | | | 2.5 | 4.08E-03 | 2.23K | | 120 |
| Propane-SH | 76.17 | | | 0.1667 | 2.72E-04 | 0.021 | 0.841 | 24.626 |
| $NaBH_4$ | 37.83 | | | 10 | 1.63E-02 | .65 g | | 41 |

As discussed, the synthesis was performed as previously described in Hostetler et al. *LANGMUIR* (1998) 14:17–30 (33). After a reaction time of about 12 hours, the crude product was concentrated in vacuo (<60° C.) and precipitated twice from a large excess of ethanol ( approximately 400 mL). The isolated black precipitate was used without further purification.

In the sensors below, "PEVA 25" is poly(ethylene-co-vinyl acetate 25% vinylacetate); PS is poly(styrene); PMMA is poly(methyl methacrylate); PVPyrolidone is polyvinylpyrolidone; PCL is polycaprolactone; and polyethylenimine is linear polyethylenimine. The sensors were fabricated on polished capacitors by the suspension casting methods described above.

TABLE 4

| Sensor | | polymer | (mg) | Solvent | (mL) | Conc. (mg/ml) | "gold" (mg) | Target polymer (mg) | Target polymer (mL) |
|---|---|---|---|---|---|---|---|---|---|
| 1; 11 | A | PEVA 25 | 170 | Toluene | 20 | 8.5 | 23.2 | 2.577 | 0.303 |
| 2; 12 | C | PS | 141 | Toluene | 20 | 7.05 | 23.2 | 2.577 | 0.365 |
| 3; 13 | F | PMMA | 185 | THF | 20 | 9.25 | 23.2 | 2.577 | 0.278 |
| 4; 14 | P | PVPyrolidone | 100 | Ethanol | 20 | 5 | 23.2 | 2.577 | 0.515 |
| 5; 15 | L | PCL | 150 | Toluene | 20 | 7.5 | 23.2 | 2.577 | 0.343 |
| 6; 16 | R | Polyethylenimine | 105 | Ethanol | 15 | 7 | 23.2 | 2.577 | 0.368 |
| 7; 17 | | None | | | | | | | | ii. Results of 5% saturation vapor of analyte and 10 exposures, ΔR/R

| sensor number | 1 | 2 | 3 | 4 | 5 | 6 | 7 |
|---|---|---|---|---|---|---|---|
| benzene | | | | | | | |
| Average | 0.05672904 | 0.05718038 | 0.03713099 | 0.03563599 | 0.02673985 | 0.01901351 | 0.01215059 |
| Stdev | 0.0088072 | 0.00243782 | 0.00442105 | 0.03755568 | 0.00315499 | 0.00170586 | 0.00214352 |
| toluene | | | | | | | |
| Average | 0.06837353 | 0.06053369 | 0.04582165 | 0.04233825 | 0.03035613 | 0.02256229 | 0.01707436 |
| Stdev | 0.00433174 | 0.00651897 | 0.00457412 | 0.05544662 | 0.00750764 | 0.00144145 | 0.00202571 |
| m-xylene | | | | | | | |
| Average | 0.06984093 | 0.0555617 | 0.05217876 | 0.02436924 | 0.03663781 | 0.02393508 | 0.02059151 |
| Stdev | 0.00140225 | 0.00357344 | 0.00091163 | 0.0091468 | 0.00119657 | 0.00047213 | 0.00085613 |
| o-xylene | | | | | | | |
| Average | 0.07166558 | 0.04837939 | 0.05199948 | 0.02092825 | 0.03721334 | 0.02306403 | 0.02094237 |
| Stdev | 0.00405308 | 0.00214992 | 0.00200939 | 0.01786382 | 0.00140922 | 0.00095604 | 0.00153367 |

| sensor number | 11 | 12 | 13 | 14 | 15 | 16 | 17 |
|---|---|---|---|---|---|---|---|
| benzene | | | | | | | |
| Average | 0.01878886 | 0.01258975 | 0.00650416 | 0.0020327 | 0.00832734 | 0.00875545 | 0.00363301 |
| Stdev | 0.00329682 | 0.00042475 | 0.000734 | 0.00201836 | 0.00198524 | 0.00104119 | 0.00080197 |
| toluene | | | | | | | |
| Average | 0.02437261 | 0.01287504 | 0.00905139 | 0.0034077 | 0.01126709 | 0.01145163 | 0.0056044 |
| Stdev | 0.00307503 | 0.0003761 | 0.00070383 | 0.00090473 | 0.00187886 | 0.00100853 | 0.00078252 |
| m-xylene | | | | | | | |
| Average | 0.02569632 | 0.01028668 | 0.01082169 | 0.00298597 | 0.0121948 | 0.01268389 | 0.00706267 |
| Stdev | 0.00121592 | 0.00022425 | 0.00027543 | 0.0148297 | 0.00107619 | 0.00077306 | 0.00058149 |
| o-xylene | | | | | | | |
| Average | 0.02669483 | 0.0087378 | 0.01078242 | 0.00379222 | 0.01293974 | 0.01244728 | 0.0073844 |
| Stdev | 0.00196557 | 0.0002382 | 0.00056744 | 0.00145561 | 0.00132586 | 0.00100642 | 0.00073839 |

Example 4 i. Polymer Synthesis. Poly(pyrrole) films used for conductivity, electrochemical, and optical measurements were prepared by injecting equal volumes of N$_2$-purged solutions of pyrrole (1.50 mmoles in 4.0 ml dry tetrahydrofuran) and phosphomolybdic acid (0.75 mmoles in 4.0 ml tetrahydrofuran) into a N$_2$-purged test tube. Once the two solutions were mixed, the yellow phosphomolybdic acid solution turned dark green, with no observable precipitation for several hours. This solution was used for film preparation within an hour of mixing.

ii Sensor Fabrication. Poly(pyrrole) sensors were made by mixing two solutions, one of which contained 0.29 mmoles pyrrole in 5.0 ml tetrahydrofuran, with the other containing 0.25 mmoles phosphomolybdic acid and 30 mg of non-conducting organic material (e.g., a polymer) in 5.0 ml of tetrahydrofuran. The mixture of these two solutions resulted in a w:w ratio of pyrrole to polymer of 2:3. An inexpensive, quick method for creating the chemiresistor array elements was accomplished by effecting a cross-sectional cut through commercial 22 nF ceramic capacitors (Kemet Electronics Corporation). Mechanical slices through these capacitors revealed a series of interdigitated metal lines (25% Ag:75% Pt), separated by 15 µm, that could be readily coated with conducting polymer. The monomer—organic material—oxidant solutions were then used to dip coat interdigitated electrodes in order to provide a robust electrical contact to the polymerized organic films. After polymerization was complete, the film was insoluble and was rinsed with solvent (tetrahydrofuran or methanol) to remove residual phosphomolybdic acid and unreacted monomer. The sensors were then connected to a commercial electrical connector block, with the resistances of the various "chemiresistor" elements readily monitored by use of a multiplexing digital ohmmeter.

iii Instrumentation. Optical spectra were obtained on a Hewlett Packard 8452A spectrophotometer, interfaced to an IBM XT. Electrochemical experiments were performed using a Princeton Applied Research Inc. 173 potentiostat/175 universal programmer. All electrochemical experiments were performed with a Pt flag auxiliary and a Saturated Calomel reference Electrode (SCE). Spin-coating was performed on a Headway Research Inc. photoresist spin coater. Film thicknesses were determined with a Dektak Model 3030 profilometer. Conductivity measurements were performed with an osmium-tipped four point probe (Alessi Instruments Inc., tip spacing=0.050", tip radii=0.010"). Transient resistance measurements were made with a conventional multimeter (Fluke Inc., "Hydra Data Logger" Meter).

Principle Component Analysis and Multi-linear Least Square Fits. A data set obtained from a single exposure of the array to an odorant produced a set of descriptors (i.e., resistances), $d_i$. The data obtained from multiple exposures thus produced a data matrix D where each row, designated by j, consisted of n descriptors describing a single member of the data set (i.e., a single exposure to an odor). Since the baseline resistance and the relative changes in resistance varied among sensors, the data matrix was autoscaled before further processing (19). In this preprocessing technique, all the data associated with a single descriptor (i.e., a column in the data matrix) were centered around zero with unit standard deviation $$d'_{ij}=(d_{ij}-d_i)/\sigma_i \tag{1}$$

where $d_i$ is the mean value for descriptor i and $\sigma_i$ is the corresponding standard deviation.

Principle component analysis (19) was performed to determine linear combinations of the data such that the maximum variance [defined as the square of the standard deviation] between the members of the data set was obtained in n mutually orthogonal dimensions. The linear combinations of the data resulted in the largest variance [or separation] between the members of the data set in the first principle component (pc1) and produced decreasing magnitudes of variance from the second to the n$^{th}$ principle component (pc2–pcn). The coefficients required to transform the autoscaled data into principle component space (by linear combination) were determined by multiplying the data matrix, D, by its transpose, D$^T$ (i.e., diagonalizing the matrix) (19)

$$R=D^T \cdot D \tag{2}$$

This operation produced the correlation matrix, R, whose diagonal elements were unity and whose off-diagonal elements were the correlation coefficients of the data. The total variance in the data was thus given by the sum of the diagonal elements in R. The n eigenvalues, and the corresponding n eigenvectors, were then determined for R. Each eigenvector contained a set of n coefficients which were used to transform the data by linear combination into one of its n principle components. The corresponding eigenvalue yielded the fraction of the total variance that was contained in that principle component. This operation produced a principle component matrix, P, which had the same dimensions as the original data matrix. Under these conditions, each row of the matrix P was still associated with a particular odor and each column was associated with a particular principle component.

Since the values in the principle component space had no physical meaning, it was useful to express the results of the principle component analysis in terms of physical parameters such as partial pressure and mole fraction. This was achieved via a multi-linear least square fit between the principle component values and the corresponding parameter of interest. A multi-linear least square fit resulted in a linear combination of the principle components which yielded the best fit to the corresponding parameter value. Fits were achieved by appending a column with each entry being unity to the principle component matrix P, with each row, j, corresponding to a different parameter value (e.g., partial pressure), $v_j$, contained in vector V. The coefficients for the best multi-linear fit between the principle components and parameter of interest were obtained by the following matrix operation $$C=(P^T \cdot P)^{-1} \cdot P^T \cdot V \tag{3}$$

where C was a vector containing the coefficients for the linear combination.

A key to the ability to fabricate chemically diverse sensing elements was the preparation of processable, air stable films of electrically conducting organic polymers. This was achieved through the controlled chemical oxidation of pyrrole (PY) using phosphomolybdic acid (H$_3$PMo$_{12}$O$_{40}$) (20) in tetrahydrofuran:

$$PY \rightarrow PY^+ + e^- \tag{4}$$

$$2PY^+ \rightarrow PY_2 + 2H^+ \tag{5}$$

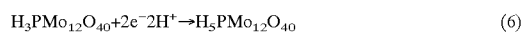

$$H_3PMo_{12}O_{40} + 2e^- 2H^+ \rightarrow H_5PMo_{12}O_{40} \tag{6}$$

The redox-driven or electrochemically-induced polymerization of pyrrole has been explored previously, but this process typically yields insoluble, intractable deposits of poly (pyrrole) as the product (21). The approach used herein was to use low concentrations of the H$_3$PMo$_{12}$O$_{40}$ oxidant (E°=+0.36 V vs. SCE) (20). Since the electrochemical potential of PY$^+$/PY is more positive (E°=+1.30 V vs. SCE)

(22) than that of $H_3PMo_{12}O_{40}/H_5PMo_{12}O_{40}$, the equilibrium concentration of PY+·, and thus the rate of polymerization, was relatively low in dilute solutions (0.19 M PY, 0.09 M $H_3PMo_{12}O_{40}$). However, it has been shown that the oxidation potential of pyrrole oligomers decreases from +1.20 V to +0.55 to +0.26 V vs. SCE as the number of units increase from one to two to three, and that the oxidation potential of bulk poly(pyrrole) occurs at −0.10 V vs. SCE (23). As a result, oxidation of pyrrole trimers by phosphomolybdic acid is expected to be thermodynamically favorable. This allowed processing of the monomer-oxidant solution (i.e., spin coating, dip coating, introduction of plasticizers, etc.), after which time polymerization to form thin films was simply effected by evaporation of the solvent. The dc electrical conductivity of poly(pyrrole) films formed by this method on glass slides, after rinsing the films with methanol to remove excess phosphomolybdic acid and/or monomer, was on the order of 15–30 S-cm$^{-1}$ for films ranging from 40–100 nm in thickness.

The poly(pyrrole) films produced in this work exhibited excellent electrochemical and optical properties. For example, FIG. 2 shows the cyclic voltammetric behavior of a chemically polymerized poly(pyrrole) film following ten cycles from −1.00 V to +0.70 V vs. SCE. The cathodic wave at −0.40 V corresponded to the reduction of poly(pyrrole) to its neutral, nonconducting state, and the anodic wave at −0.20 V corresponded to the reoxidation of poly(pyrrole) to its conducting state (24). The lack of additional faradaic current, which would result from the oxidation and reduction of phosphomolybdic acid in the film, suggests that the Keggin structure of phosphomolybdic acid was not present in the film anions (25) and implies that $MoO_4^{2-}$, or other anions, served as the poly(pyrrole) counterions in the polymerized films.

FIG. 3A shows the optical spectrum of a processed polypyrrole film that had been spin-coated on glass and then rinsed with methanol. The single absorption maximum was characteristic of a highly oxidized poly(pyrrole) (26), and the absorption band at 4.0 eV was characteristic of an interband transition between the conduction and valence bands. The lack of other bands in this energy range was evidence for the presence of bipolaron states (see, FIG. 3A), as have been observed in highly oxidized poly(pyrrole) (26). By cycling the film in 0.10 M $[(C_4H_9)_4N]^+[ClO_4]^-$— acetonitrile and then recording the optical spectra in 0.10 M $KCl—H_2O$, it was possible to observe optical transitions characteristic of polaron states in oxidized poly(pyrrole) (see, FIG. 3B). The polaron states have been reported to produce three optical transitions (26), which were observed at 2.0, 2.9, and 4.1 eV in FIG. 3B. Upon reduction of the film (c.f. FIG. 3B), an increased intensity and a blue shift in the 2.9 eV band was observed, as expected for the Π-Π* transition associated with the pyrrole units contained in the polymer backbone (27).

As described in the experimental section, various polymers were introduced into the polymer films (Table 5).

TABLE 5

Polymers used in array elements*

| Sensor | Polymers |
| --- | --- |
| 1 | None |
| 2 | none** |
| 3 | poly(styrene) |
| 4 | poly(styrene) |
| 5 | polyα(styrene) |
| 6 | poly(α-methyl styrene) |
| 7 | poly(styrene-acrylonitrile) |

TABLE 5-continued

Polymers used in array elements*

| Sensor | Polymers |
| --- | --- |
| 8 | poly(styrene-maleic anhydride) |
| 9 | poly(styrene-allyl alcohol) |
| 10 | poly(vinyl pyrrolidone) |
| 11 | poly(vinyl phenol) |
| 12 | poly(vinyl butral) |
| 13 | poly(vinyl acetate) |
| 14 | poly(carbonate) |

*Sensors contained 2:3 (w:w) ratio of pyrrole to polymer.
**Film not rinsed to remove excess phosphomolybdic acid.

These inclusions allowed chemical control over the binding properties and electrical conductivity of the resulting polymers. Sensor arrays consisted of as many as 14 different elements, with each element synthesized to produce a distinct chemical composition and, thus, a distinct sensor response for its polymer film. The resistance, R, of each film-coated individual sensor was automatically recorded before, during, and after exposure to various odorants. A typical trial consisted of a 60 sec rest period in which the sensors were exposed to flowing air (3.0 liter-min$^{-1}$), a 60 sec exposure to a mixture of air (3.0 liter-min$^{-1}$) and air that had been saturated with solvent (0.5–3.5 liter-min$^{-1}$), and then a 240 sec exposure to air (3.0 liter-min$^{-}$).

In an initial processing of the data, the only information used was the maximum amplitude of the resistance change divided by the initial resistance, $\Delta R_{max}/R_i$, of each individual sensor element. Most of the sensors exhibited either increases or decreases in resistance upon exposure to different vapors, as expected from changes in the polymer properties upon exposure to different types chemicals (17–18). However, in some cases, sensors displayed an initial decrease followed by an increase in resistance in response to a test odor. Since the resistance of each sensor could increase and/or decrease relative to its initial value, two values of $\Delta R_{max}/R_i$ were reported for each sensor. The source of the bi-directional behavior in most cases arises from the presence of water (which by itself induced rapid decreases in the film resistance) in the reagent-grade solvents used to generate the test odors of this study. The observed behavior in response to these air-exposed, water-containing test solvents was reproducible and reversible on a given sensor array, and the environment was representative of many practical odor sensing applications in which air and water would not be readily excluded.

FIGS. 4B–4D depict representative examples of sensor amplitude responses of a sensor array (see, Table 5). In this experiment, data were recorded for three separate exposures to vapors of acetone, benzene, and ethanol flowing in air. The response patterns generated by the sensor array described in Table 5 are displayed for: (B) acetone; (C) benzene; and (D) ethanol. The sensor response was defined as the maximum percent increase and decrease of the resistance divided by the initial resistance (gray bar and black bar, respectively) of each sensor upon exposure to solvent vapor. In many cases, sensors exhibited reproducible increases and decreases in resistance. An exposure consisted of: (i) a 60 sec rest period in which the sensors were exposed to flowing air (3.0 liter-min$^{-1}$); (ii) a 60 sec exposure to a mixture of air (3.0 liter-min$^{-1}$) and air that had been saturated with solvent (0.5 liter-min$^{-1}$); and (iii) a 240 sec exposure to air (3.0 liter-min$^{-1}$). It is readily apparent that these odorants each produced a distinctive response on the sensor array. In additional experiments, a total of 8 separate vapors (acetone, benzene, chloroform, ethanol, isopropyl alcohol, methanol, tetrahydrofuran, and ethyl acetate), chosen to span a range of chemical and physical characteristics, were evaluated over a five-day period on a 14-element sensor array (Table 5). As discussed below, each odorant could be clearly and reproducibly identified from the others using this sensor apparatus.

Principle component analysis (19) was used to simplify presentation of the data and to quantify the distinguishing abilities of individual sensors and of the array as a whole. In this approach, linear combinations of the $\Delta R_{max}/R_i$ data for the elements in the array were constructed such that the maximum variance (defined as the square of the standard deviation) was contained in the fewest mutually orthogonal dimensions. This allowed representation of most of the information contained in data sets shown in FIGS. 4B–4D in two (or three) dimensions. The resulting clustering, or lack thereof, of like exposure data in the new dimensional space was used as a measure of the distinguishing ability, and of the reproducibility, of the sensor array.

In order to illustrate the variation in sensor response of individual sensors that resulted from changes in the polymer, principle component analysis was performed on the individual, isolated responses of each of the 14 individual sensor elements in a typical array (FIG. 5). Data were obtained from multiple exposures to acetone (a), benzene (b), chloroform (c), ethanol (e), isopropyl alcohol (i), methanol (m), tetrahydrofuran (+), or ethyl acetate (@) over a period of five days with the test vapors exposed to the array in various sequences. The numbers of the figures refer to the sensor elements described in Table 5. The units along the axes indicate the amplitude of the principle component that was used to describe the particular data set for an odor. The black regions indicate clusters corresponding to a single solvent which could be distinguished from all others; gray regions highlight data of solvents whose signals overlapped with others around it. Exposure conditions were identical to those in FIG. 4.

Since each individual sensor produced two data values, principle component analysis of these responses resulted in only two orthogonal principal components: pc1 and pc2. As an example of the selectivity exhibited by an individual sensor element, the sensor designated as number 5 in FIG. 5 (which comprised poly(styrene)) confused acetone with chloroform, isopropyl alcohol, and tetrahydrofuran. It also confused benzene with ethyl acetate, while easily distinguishing ethanol and methanol from all other solvents. Changing the polymer to poly (α-methyl styrene) (sensor number 6 in FIG. 5) had little effect on the spatial distribution of the responses with respect to one another and with respect to the origin. Thus, as expected, a rather slight chemical modification of the polymer had little effect on the relative variance of the eight test odorants. In contrast, the addition of a cyano group in the form of poly(styrene-acrylonitrile) (sensor number 7 in FIG. 5) resulted in a larger contribution to the overall variance by benzene and chloroform, while decreasing the contribution of ethanol. Changing the substituent group in the polymer to a hydrogen bonding acid (poly(styrene-allyl alcohol), sensor number 9 in FIG. 5) increased the contribution of acetone to the overall variance while having little effect on the other odors, with the exception of confusing methanol and ethanol. These results suggest that the behavior of the sensors can be systematically altered by varying the chemical composition of the polymer.

FIG. 6 shows the principle component analysis for all 14 sensors described in Table 5 and FIGS. 4 and 5. When the solvents were projected into a three dimensional odor space (FIG. 6A or 6B), all eight solvents were easily distinguished with the specific array discussed herein. Detection of an individual test odor, based only on the criterion of observing ~1% $\Delta R_{max}/R_i$ values for all elements in the array, was readily accomplished at the parts per thousand level with no control over the temperature or humidity of the flowing air.

Further increases in sensitivity are likely after a thorough utilization of the temporal components of the $\Delta R_{max}/R_i$ data as well as a more complete characterization of the noise in the array.

The suitability of this sensor array for identifying the components of certain test mixtures has also been investigated. This task is greatly simplified if the array exhibits a predictable signal response as the concentration of a given odorant is varied, and if the responses of various individual odors are additive (i.e., if superposition is maintained). When a 19-element sensor array was exposed to a number, n, of different acetone concentrations in air, the $(CH_3)_2CO$ concentration was semi-quantitatively predicted from the first principle component. This was evident from a good linear least square fit through the first three principle components.

The same sensor array was also able to resolve the components in various test methanol-ethanol mixtures (29). As shown in FIG. 7B, a linear relationship was observed between the first principle component and the mole fraction of methanol in the liquid phase, $x_m$, in a $CH_3OH$—$C_2H_5OH$ mixture, demonstrating that superposition held for this mixture/sensor array combination. Furthermore, although the components in the mixture could be predicted fairly accurately from just the first principle component, an increase in the accuracy could be achieved using a multilinear least square fit through the first three principle components. This relationship held for $CH_3OH/(CH_3OH+C_2H_5OH)$ ratios of 0 to 1.0 in air-saturated solutions of this vapor mixture. The conducting polymer-based sensor arrays could therefore not only distinguish between pure test vapors, but also allowed analysis of concentrations of odorants as well as analysis of binary mixtures of vapors.

In summary, the results presented herein advance the area of analyte sensor design. A relatively simple array design, using only a multiplexed low-power dc electrical resistance readout signal, has been shown to readily distinguish between various test odorants. Such conducting polymer-based arrays are simple to construct and modify, and afford an opportunity to effect chemical control over the response pattern of a vapor. For example, by changing the ratio of polymer to conducting particle, it is possible to approach the percolation threshold, at which point the conductivity exhibits a very sensitive response to the presence of the sorbed molecules. Furthermore, producing thinner films will afford the opportunity to obtain decreased response times, and increasing the number of polymers and polymer backbone motifs will likely result in increased diversity among sensors. This type of polymer-based array is chemically flexible, is simple to fabricate, modify, and analyze, and utilizes a low power dc resistance readout signal transduction path to convert chemical data into electrical signals. It provides a new approach to broadly-responsive odor sensors for fundamental and applied investigations of chemical mimics for the mammalian sense of smell. Such systems are useful for evaluating the generality of neural network algorithms developed to understand how the mammalian olfactory system identifies the directionality, concentration, and identity of various odors.

Example 4

Fabrication and Testing of Carbon Black-based Sensor Arrays i. Sensor Fabrication. Individual sensor elements were fabricated in the following manner. Each non-conductive polymer (80 mg, see Table 6) was dissolved in 6 ml of THF.

TABLE 6

| Sensor # | Non-Conductive Polymer |
| --- | --- |
| 1 | poly(4-vinyl phenol) |
| 2 | poly(styrene-allyl alcohol) |
| 3 | poly(α-methyl styrene) |
| 4 | poly(vinyl chloride-vinyl acetate) |
| 5 | poly(vinyl acetate) |
| 6 | poly(N-vinyl pyrrolidone) |
| 7 | poly(bisphenol A carbonate) |
| 8 | poly(styrene) |
| 9 | poly(styrene-maleic anhydride) |
| 10 | poly(sulfone) |

Then, 20 mg of carbon black (BP 2000, Cabot Corp.) were suspended with vigorous mixing. Interdigitated electrodes (the cleaved capacitors previously described) were then dipped into this mixture and the solvent allowed to evaporate. A series of such sensor elements with differing nonconductive polymers were fabricated and incorporated into a commercial bus strip which allowed the chemiresistors to be easily monitored with a multiplexing ohmmeter.

ii. Sensor Array Testing. To evaluate the performance of the carbon-black based sensors, arrays with as many as 20 elements were exposed to a series of analytes. A sensor exposure consisted of (1) a 60 second exposure to flowing air (6 liter min−1), (2) a 60 second exposure to a mixture of air (6 liter min−1) and air that had been saturated with the analyte (0.5 liter min−1) and (3) a five minute recovery period during which the sensor array was exposed to flowing air (6 liter min−1). The resistance of the elements were monitored during exposure, and depending on the thickness and chemical make-up of the film, resistance changes as large as 250% could be observed in response to an analyte. In one experiment, a 10 element sensor array consisting of carbon-black composites formed with a series of nonconductive polymers (see, Table 6) was exposed to acetone, benzene, chloroform, ethanol, hexane, methanol, and toluene over a two day period. A total of 58 exposures to these analytes were performed in this time period. In all cases, resistance changes in response to the analytes were positive, and with the exception of acetone, reversible (see, FIG. 8). The maximum positive deviations were then subjected to principal component analysis in a manner analogous to that described for the poly(pyrrole) based sensor. FIG. 9 shows the results of the principal component analysis for the entire 10-element array. With the exception of overlap between toluene with benzene, the analytes were distinguished from one and other.

Cited References: 1. Lundström et al. (1991) *Nature* 352:47–50; 2. Shurmer and Gardner (1992) *Sens. Act. B* 8: 1–11; 3. Reed (1992) *Neuron* 8:205–209; 4. Lancet and Ben-Airie (1993) *Curr. Biol.* 3:668–674; 5. Kauer (1991) *TINS* 14:79–85; 6. DeVries and Baylor (1993) *Cell* 10(S):139–149; 7. Gardner et al. (1991) *Sens. Act. B* 4:117–121; 8. Gardner et al. (1991) *Sens. Act. B* 6:71–75; 9. Corcoran et al. (1993) *Sens. Act. B* 15:32–37; 10. Grate and Abraham (1991) *Sens. Act. B* 3:85–111; 11. Grate et al. (1993) *Anal. Chem.* 65:1868–1881; 12. Stetter et al. (1986) *Anal. Chem.* 58:860–866; 13. Stetter et al. (1990) *Sens. Act. B* 1:43–47; 14. Stetter et al. (1993) *Anal. Chem. Acta* 284: 1–11; 15. Pearce et al. (1993) *Analyst* 118:371–377; 16. Shurmer et al. (1991) *Sens. Act. B* 4:29–33; 17. Topart and Josowicz (1992) *J. Phys. Chem.* 96:7824–7830; 18. Charlesworth et al. (1993) *J. Phys. Chem.* 97:5418–5423; 19. Hecht (1990) *Mathematics in Chemistry: An Introduction to Modern Methods* (Prentice Hall, Englewood Cliffs, N.J.); 20. Pope (1983) *Heteropoly and Isopoly Oxometalates* (Springer-Verlag, New York), chap. 4; 21. Salmon et al. (1982) *J. Polym. Sci., Polym. Lett.* 20:187–193; 22. Andrieux et al. (1990) *J. Am. Chem. Soc.* 112:2439–2440; 23. Diaz et al. (1981) *J. Electroanal Chem.* 121:355–361; 24. Kanazawa et al. (1981) *Synth. Met.* 4:119–130; 25. Bidan et al. (1988) *J. Electroanal. Chem.* 251:297–306; 26. Kaufman et al. (1984) *Phys. Rev. Lett.* 53:1005–1008; 27. Yakushi et al. (1983) *J. Chem. Phys.* 79:4774–4778; and Morris et al. (1942) *Can. J. Res. B* 20:207–211. 30. Brust, M.; Walker, M.; Bethell, D.; Schiffrin, D. J.; Whyman, R. *J. Chem. Soc., Chem. Commun.,* 1994, 801–802. 31. Leff, D. V.; Ohara, P. C.; Heath, J. R.; Gelbart, W. M. *J. Phys. Chem.* 1995, 99, 7036–7041; 32. Templeton et al. *J. Am. Chem. Soc.* (1998) 120 :1906–1911; 33. Lee et al., *Isr. J. Chem.* (1997) 37: 213–223 (1997); 33. Hostetler et al. *LANGMUIR* (1998) 14:17–30; 34. Ingram et al., *J. Am. Chem. Soc.,* (1997) 119 :9175–9178; 35. Hostetler et al., *J. Am Chem. Soc.* (1996) 118:4212–4213; 36. Henglein *J. Phys. Chem.* (1993) 97:5457–5471; 37. Zeiri, *J. Phys. Chem.* (1992) 96:5908–5917; 38. Leff et al., *LANGMUIR* (1996) 4723–4730.

All publications, patents and patent applications mentioned in this specification are herein incorporated by reference into the specification to the same extent as if each individual publication, patent or patent application was specifically and individually indicated to be incorporated herein by reference.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A device for detecting a chemical analyte, said device comprising:

a sensor array connected to a measuring apparatus having at least one sensor comprising regions of nonconductive material and conductive material compositionally different than said nonconductive material, wherein said conductive material comprises a nanoparticle covalenty linked to said nonconductive material and said nonconductive material comprises a biomolecule, and a response path through said regions of nonconductive material and said conductive material.

2. A device for detecting a chemical analyte according to claim 1, wherein said nanoparticle comprises a member selected from the group consisting of an organic material, an inorganic material or a mixed inorganic-organic material.

3. A device for detecting a chemical analyte according to claim 2, wherein said nanoparticle has a core, wherein said core is a member selected from the group consisting of a metal, a metal alloy, a metal oxide, an organic complex, a semiconductor, a superconductor and a mixed inorganic-organic complex.

4. A device for detecting a chemical analyte according to claim 3, wherein said core is a metal.

5. A device for detecting a chemical analyte according to claim 4, wherein said metal is a member selected from the group consisting of Ag, Au, Cu, Pt, Pd, Ni, AuCu and mixtures thereof.

6. A device for detecting a chemical analyte according to claim 5, wherein said metal is Au.

7. A device for detecting a chemical analyte according to claim 1, wherein said biomolecule is polyfunctionalized.

8. A device for detecting a chemical analyte according to claim 1, wherein said biomolecule is ω-functionalized.

9. A device for detecting a chemical analyte according to claim 1, wherein said biomolecule selected from the group consisting of a carbohydrate, a polysaccharide, a protein complex, a polypeptide, an oligonucleotide, a fluorescent moiety, and mixtures thereof.

10. A device for detecting a chemical analyte according to claim 9, wherein said biomolecule is an oligonucleotide.

11. A device for detecting a chemical analyte to claim 1, wherein said nanoparticle comprises a gold cluster and an organic ligand.

12. A device for detecting a chemical analyte according to claim 1, wherein said measuring device is an electrical measuring device.

13. A device for detecting a chemical analyte according to claim 1, wherein said response is a member selected from the group consisting of resistance, impedance, capacitance, inductance, or a combination thereof.

14. A device for detecting a chemical analyte according to claim 1, wherein at least one sensor of said array of sensors is a member selected from the group consisting of a surface acoustic wave sensor, a quartz microbalance sensor, a conductive composite; a chemiresitor, a metal oxide gas sensor and a conducting polymer sensor, a dye-impregnated polymer film on fiber optic detector, a polymer-coated micromirror, an electrochemical gas detector, a chemically sensitive field-effect transistor, a carbon black-polymer composite, a micro-electro-mechanical system device and a micro-opto-electro-mechanical system device.

15. A device for detecting a chemical analyte according to claim 1, wherein said response path is an electrical response path that is measured to detect the chemical analyte.

* * * * *

UNITED STATES PATENT AND TRADEMARK OFFICE
CERTIFICATE OF CORRECTION

PATENT NO.    : 6,537,498 B1
DATED         : March 25, 2003
INVENTOR(S)   : Nathan S. Lewis et al.

It is certified that error appears in the above-identified patent and that said Letters Patent is hereby corrected as shown below:

<u>Title page, Item [60] and Column 1, line 15,</u>
Replace "60/088,630" with -- 60/088,680 --.

Signed and Sealed this

Thirtieth Day of September, 2003

JAMES E. ROGAN
*Director of the United States Patent and Trademark Office*